US012751605B2

(12) United States Patent
Abe et al.

(10) Patent No.: US 12,751,605 B2
(45) Date of Patent: Oct. 6, 2026

(54) MEDICAL INSTRUMENT GUIDE DEVICE AND ENDOSCOPE APPARATUS

(71) Applicant: FUJIFILM Corporation, Tokyo (JP)

(72) Inventors: Shinya Abe, Kanagawa (JP); Tatsuya Minagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 343 days.

(21) Appl. No.: 18/452,551

(22) Filed: Aug. 20, 2023

(65) Prior Publication Data

US 2023/0389783 A1 Dec. 7, 2023

Related U.S. Application Data

(63) Continuation of application No. PCT/JP2022/003292, filed on Jan. 28, 2022.

(30) Foreign Application Priority Data

Feb. 25, 2021 (JP) ................................ 2021-028421
Oct. 28, 2021 (JP) ................................ 2021-176105

(51) Int. Cl.
*A61B 1/00* (2006.01)
*A61B 1/01* (2006.01)
*A61M 25/00* (2006.01)
*A61M 25/01* (2006.01)
*A61M 25/06* (2006.01)

(52) U.S. Cl.
CPC ........... *A61B 1/01* (2013.01); *A61M 25/0045* (2013.01); *A61M 25/0138* (2013.01); *A61M 25/0155* (2013.01); *A61M 2025/0681* (2013.01)

(58) Field of Classification Search
CPC .. A61B 1/01; A61B 1/00071; A61M 25/0045; A61M 25/0138; A61M 25/0155; A61M 2025/0681
See application file for complete search history.

(56) References Cited

U.S. PATENT DOCUMENTS 3,998,216 A * 12/1976 Hosono ................ A61B 1/0055 600/182
5,337,733 A * 8/1994 Bauerfeind ........ A61B 1/00078 604/524
6,398,791 B1 6/2002 Que et al.
(Continued)

FOREIGN PATENT DOCUMENTS

CN 107206213 9/2017
CN 109068941 12/2018
(Continued)

OTHER PUBLICATIONS

"Search Report of Europe Counterpart Application", issued on Jun. 20, 2024, p. 1-p. 6.
(Continued)

*Primary Examiner* — Timothy J Neal
(74) *Attorney, Agent, or Firm* — JCIPRNET

(57) ABSTRACT

A medical instrument guide device includes a tube main body (606) that includes an outer tube (602) having flexibility and an inner tube (604) having flexibility and being arranged inside the outer tube (602), and a shape deformable body (612) that is provided between the outer tube (602) and the inner tube (604) and is deformable along a shape of the tube main body (606).

19 Claims, 29 Drawing Sheets

(56) References Cited

U.S. PATENT DOCUMENTS

| | | | |
|---|---|---|---|
| 6,939,353 B2 | 9/2005 | Que et al. | |
| RE47,285 E | 3/2019 | Loske | |
| 2005/0159644 A1* | 7/2005 | Takano | A61B 1/00082 600/116 |
| 2005/0272975 A1* | 12/2005 | McWeeney | A61B 1/307 600/172 |
| 2005/0277949 A1 | 12/2005 | Que et al. | |
| 2010/0069716 A1 | 3/2010 | Chin et al. | |
| 2011/0004157 A1 | 1/2011 | Dewaele et al. | |
| 2011/0237888 A1 | 9/2011 | Matsushita | |
| 2018/0042458 A1 | 2/2018 | Araki | |
| 2019/0046012 A1 | 2/2019 | Ikeda | |
| 2020/0178763 A1 | 6/2020 | Tilson et al. | |
| 2020/0275983 A1 | 9/2020 | Dewaele et al. | |
| 2021/0129510 A1 | 5/2021 | Inomata et al. | |
| 2025/0169678 A1 | 5/2025 | Tilson et al. | |

FOREIGN PATENT DOCUMENTS

| | | |
|---|---|---|
| CN | 112367895 | 2/2021 |
| EP | 3266487 | 10/2022 |
| JP | H05503434 | 6/1993 |
| JP | 2003501197 | 1/2003 |
| JP | 2005046278 | 2/2005 |
| JP | 2005278846 | 10/2005 |
| JP | 2009082455 | 4/2009 |
| JP | 2011194126 | 10/2011 |
| JP | 2012024597 | 2/2012 |
| JP | 2014512896 | 5/2014 |
| JP | 3204367 | 6/2016 |
| JP | 2020527985 | 9/2020 |
| WO | 2016185842 | 11/2016 |
| WO | 2020017534 | 1/2020 |

OTHER PUBLICATIONS

“Notice of Reasons for Refusal of Japan Counterpart Application”, issued on Jul. 14, 2025, with English translation thereof, p. 1-p. 14.

“Notice of Reasons for Refusal of Japan Counterpart Application”, issued on Oct. 1, 2025, with English translation thereof, p. 1-p. 14.

“International Search Report (Form PCT/ISA/210) of PCT/JP2022/003292,” mailed on Apr. 5, 2022, with English translation thereof, pp. 1-7.

“Written Opinion of the International Searching Authority (Form PCT/ISA/237) of PCT/JP2022/003292,” mailed on Apr. 5, 2022, with English translation thereof, pp. 1-8.

“Decision of Refusal of Japan Counterpart Application”, issued on Jan. 8, 2026, with English translation thereof, p. 1-p. 8.

“The First Office Action of China Counterpart Application”, issued on Jan. 19, 2026, with English translation thereof, pp. 1-17.

“The Rejection Decision of China Counterpart Application”, issued on May 26, 2026, with English translation thereof, p. 1-p. 21.

* cited by examiner

MEDICAL INSTRUMENT GUIDE DEVICE AND ENDOSCOPE APPARATUS

CROSS-REFERENCE TO RELATED APPLICATIONS

The present application is a Continuation of PCT International Application No. PCT/JP2022/003292 filed on Jan. 28, 2022 claiming priorities under 35 U.S.C § 119(a) to Japanese Patent Application No. 2021-028421 filed on Feb. 25, 2021 and Japanese Patent Application No. 2021-176105 filed on Oct. 28, 2021. Each of the above applications is hereby expressly incorporated by reference, in its entirety, into the present application.

BACKGROUND OF THE INVENTION

1. Field of the Invention

The present invention relates to a medical instrument guide device that guides a medical instrument, such as an insertion part of an endoscope, into a body and an endoscope apparatus.

2. Description of the Related Art

An insertion part of an endoscope (hereinafter, also referred to as an "endoscope insertion part") is inserted along a winding and flexible insertion path such as an upper digestive tract or a lower digestive tract. Therefore, the endoscope insertion part has the flexibility that can be inserted along the insertion path.

However, since the intestinal tract, which is an example of the insertion path, has a portion that is not fixed to the body (for example, a sigmoid colon) and the above-described portion is deformed in the middle even though the insertion part is pushed during insertion of the endoscope insertion part, there is a problem that it is difficult for a distal end part of the insertion part to move forward. Further, there is a case where a treatment tool is led out from the distal end part of the insertion part to perform a precise operation of cutting out a lesion portion during treatment of the endoscope, but there is a case where the deformation of the above-described portion interferes with the precise operation.

Therefore, JP2011-194126A discloses a guide tube for eliminating an unstable operation during the insertion and the treatment. The guide tube disclosed in JP2011-194126A has a configuration in which a long muscle body having an engagement surface and a strength holding member is arranged in a sealed space between an inner tube and an outer tube having the flexibility, a fluid is discharged from the sealed space to press the engagement surface against at least one of the inner tube or the outer tube into a pressed state, and the fluid is supplied into the sealed space to release the pressed state. With this guide tube, a change in hardness between a flexible state in a bending direction and a high stiffness property state can be caused.

SUMMARY OF THE INVENTION

However, in a case where the hardness of the guide tube (medical instrument guide device) as in JP2011-194126A is changed to the high stiffness property state, it is difficult to sufficiently secure a contact area between the engagement surface of the muscle body and the inner tube or the outer tube. For this reason, it is difficult to hold the shape of the medical instrument guide device in a bent shape along a bending part of the intestinal tract, and thus there is a problem in that the insertability of the medical instrument such as the endoscope insertion part or the treatment tool decreases. On the other hand, in a case where the number of the muscle bodies is increased, the contact area can be sufficiently secured. However, in this case, there is a problem in that the flexibility of the medical instrument guide device is impaired, and thus the insertability of the medical instrument decreases.

The present invention has been made in view of such circumstances, and is to provide a medical instrument guide device and an endoscope apparatus that can improve the insertability of a medical instrument.

In order to solve the above problems, an aspect of the present invention relates to a medical instrument guide device that guides a medical instrument into a body, the medical instrument guide device comprising a tube main body that includes an outer tube having flexibility and an inner tube having flexibility and being arranged inside the outer tube, and a shape deformable body that is provided between the outer tube and the inner tube and is deformable along a shape of the tube main body.

According to the aspect of the present invention, it is preferable that the medical instrument guide device further comprises an interlayer that is provided between the outer tube and the inner tube and is contactable with the shape deformable body, in which a first contact surface that is provided on the shape deformable body and a second contact surface that is provided on the interlayer and faces the first contact surface are provided, and at least a part of any one contact surface of the first contact surface or the second contact surface includes a high friction surface.

According to the aspect of the present invention, it is preferable that the interlayer is provided between the outer tube and the shape deformable body.

According to the aspect of the present invention, it is preferable that the high friction surface is provided on the second contact surface.

According to the aspect of the present invention, it is preferable that the high friction surface is provided on the first contact surface.

According to the aspect of the present invention, it is preferable that the interlayer has a higher elastic modulus than the outer tube and the inner tube.

According to the aspect of the present invention, it is preferable that the interlayer is formed by forming a sheet material into a cylindrical shape.

According to the aspect of the present invention, it is preferable that the medical instrument guide device further comprises a fluid supply and discharge unit that supplies and discharges a fluid to and from an inner space between the outer tube and the inner tube, in which, in a case where the fluid in the inner space is discharged by the fluid supply and discharge unit, in the tube main body, a shape of the shape deformable body is held by frictional engagement between the shape deformable body and the interlayer via the high friction surface.

According to the aspect of the present invention, it is preferable that a first contact surface that is provided on the shape deformable body and a second contact surface that is provided on at least one tube of the outer tube or the inner tube and faces the first contact surface are provided, and at least a part of any one contact surface of the first contact surface or the second contact surface includes a high friction surface.

According to the aspect of the present invention, it is preferable that the medical instrument guide device further comprises a fluid supply and discharge unit that supplies and discharges a fluid to and from an inner space between the outer tube and the inner tube, in which, in a case where the fluid in the inner space is discharged by the fluid supply and discharge unit, in the tube main body, a shape of the shape deformable body is held by frictional engagement between the shape deformable body and the one tube via the high friction surface.

According to the aspect of the present invention, it is preferable that the high friction surface is a resin layer in which the one contact surface is coated with a resin.

According to the aspect of the present invention, it is preferable that the high friction surface is a rough surface formed on the one contact surface.

According to the aspect of the present invention, it is preferable that the high friction surface is a resin layer in which a rough surface formed on the one contact surface is coated with a resin.

According to the aspect of the present invention, it is preferable that the shape deformable body includes a spiral tube formed by spirally winding a band-shaped member around an outer peripheral side of the inner tube.

According to the aspect of the present invention, it is preferable that the shape deformable body includes a plurality of articulated ring members that are arranged along an axial direction of the tube main body, and the articulated ring member includes a fixing ring member that has an annular shape and is provided such that a relative position thereof in the axial direction with respect to the outer tube or the inner tube is fixable, and a plurality of articulated pieces that extend in a comb teeth shape from the fixing ring member to at least one side in the axial direction and are arranged side by side in a circumferential direction around the axial direction.

According to the aspect of the present invention, it is preferable that the articulated ring member includes a plurality of articulated pieces that each extend from the fixing ring member to both sides in the axial direction.

According to the aspect of the present invention, it is preferable that, in a case where the articulated ring members, which are adjacent to each other in the axial direction among the plurality of articulated ring members, are defined as a first articulated ring member and a second articulated ring member, the articulated piece of the first articulated ring member, which extends to a side of the second articulated ring member, is defined as a first articulated piece, and the articulated piece of the second articulated ring member, which extends to a side of the first articulated ring member, is defined as a second articulated piece, a first articulated piece end part region of the first articulated piece on the side of the second articulated ring member and a second articulated piece end part region of the second articulated piece on the side of the first articulated ring member are arranged at positions at which positions thereof in the axial direction overlap each other, and are arranged at positions at which positions thereof in the circumferential direction are shifted from each other.

According to the aspect of the present invention, it is preferable that the first articulated piece and the second articulated piece are alternately arranged one by one along the circumferential direction.

According to the aspect of the present invention, it is preferable that a plurality of first articulated piece groups consisting of two or more of the first articulated pieces and a plurality of second articulated piece groups consisting of two or more of the second articulated pieces are alternately arranged along the circumferential direction.

According to the aspect of the present invention, it is preferable that, in a case where the articulated ring members, which are adjacent to each other in the axial direction among the plurality of articulated ring members, are defined as a first articulated ring member and a second articulated ring member, the articulated piece of the first articulated ring member, which extends to a side of the second articulated ring member, is defined as a first articulated piece, and the articulated piece of the second articulated ring member, which extends to a side of the first articulated ring member, is defined as a second articulated piece, the first articulated piece and the second articulated piece are arranged at positions at which positions thereof in the axial direction are shifted from each other, and are arranged at positions at which positions thereof in the circumferential direction are shifted from each other.

According to the aspect of the present invention, it is preferable that, in a case where a width of the articulated ring member in the axial direction is denoted by W1 and an arrangement pitch of the articulated ring members in the axial direction is denoted by P, the following expression is satisfied, which is represented by $P<W1$.

According to the aspect of the present invention, it is preferable that, in a case where a width of the articulated ring member in the axial direction is denoted by W1 and an arrangement pitch of the articulated ring members in the axial direction is denoted by P, the following expression is satisfied, which is represented by $P>W1$.

According to the aspect of the present invention, it is preferable that the plurality of articulated pieces that are arranged side by side in the circumferential direction are arranged at equal intervals along the circumferential direction.

According to the aspect of the present invention, it is preferable that the plurality of fixing ring members are arranged at equal intervals along the axial direction.

According to the aspect of the present invention, it is preferable that the articulated piece includes a piece body that has a rectangular shape and is formed to be elongated in the axial direction, and a coupling member that is provided between the piece body and the fixing ring member and is formed to be narrower than the piece body.

According to the aspect of the present invention, it is preferable that at least one surface of an outer peripheral surface of the outer tube or an inner peripheral surface of the inner tube has a hydrophilic coating.

According to the aspect of the present invention, it is preferable that the medical instrument is an endoscope having an insertion part to be inserted into the body.

According to the aspect of the present invention, it is preferable that the medical instrument guide device further comprises a switching member that is able to switch between opening to the atmosphere and inflow of the atmosphere with respect to an inner space positioned between the outer tube and the inner tube.

According to the aspect of the present invention, it is preferable that the tube main body includes an intracorporeal close attachment part provided at a distal end part of the tube main body.

According to the aspect of the present invention, it is preferable that the intracorporeal close attachment part includes a tube main body balloon that is expandable and contractible and is arranged at the distal end part of the tube main body.

According to the aspect of the present invention, it is preferable that the intracorporeal close attachment part includes a suction port that is arranged at the distal end part of the tube main body.

According to the aspect of the present invention, it is preferable that the intracorporeal close attachment part includes a porous entanglement prevention member that covers the suction port.

In order to solve the above problems, another aspect of the present invention relates to an endoscope apparatus comprising the medical instrument, and the medical instrument guide device according to the aspect of the present invention, in which the medical instrument is an endoscope having an insertion part to be inserted into a body.

According to the aspect of the present invention, it is preferable that the endoscope includes a switching unit that is able to switch between opening to the atmosphere and inflow of the atmosphere with respect to an inner space positioned between the outer tube and the inner tube.

According to the aspect of the present invention, it is preferable that the insertion part is able to be inserted into the tube main body, and in a state in which the insertion part is inserted into the tube main body, a clearance for preventing a body tissue from being interposed is formed between the tube main body and the insertion part.

According to the aspect of the present invention, it is preferable that the clearance is 4 mm or less.

According to the aspect of the present invention, it is preferable that the insertion part has an effective length that is longer than an entire length of the tube main body by 300 mm or more.

According to the aspect of the present invention, it is preferable that the insertion part includes an insertion part balloon that is expandable and contractible and is provided at a distal end part of the insertion part.

According to the present invention, the insertability of the medical instrument can be improved.

DESCRIPTION OF THE PREFERRED EMBODIMENTS

Hereinafter, embodiments of a medical instrument guide device and an endoscope apparatus of the present invention will be described with reference to the accompanying drawings.

Figure 1:
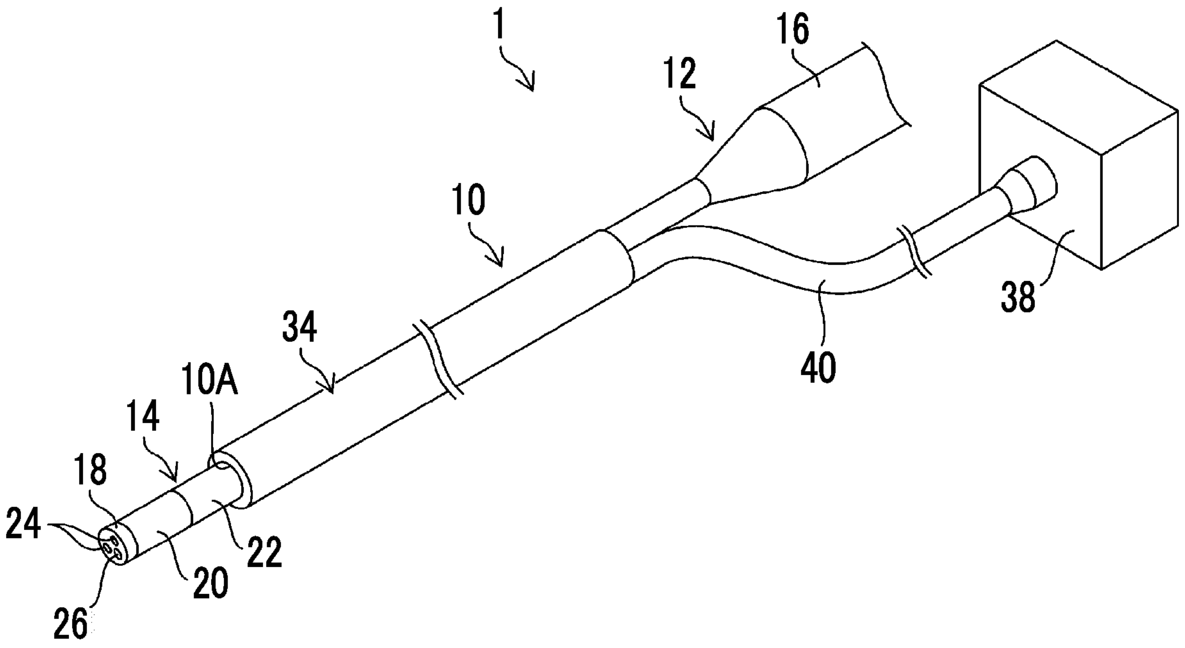
FIG. 1 shows an external view of an endoscope apparatus according to a first embodiment of the present invention.

FIG. 1 is an external view of an endoscope apparatus 1 according to a first embodiment of the present invention. As shown in FIG. 1, an endoscope apparatus 1 comprises a medical instrument guide device (hereinafter, referred to as a "guide tube") 10 according to the first embodiment and an endoscope 12. FIG. 1 shows a usage form in which an insertion part 14 of the endoscope 12 is inserted into the guide tube 10. In FIG. 1, the endoscope 12 includes the insertion part 14 and a hand operating part 16, and a proximal end side of the insertion part 14 is coupled to the hand operating part 16. Here, the endoscope 12 having the insertion part 14 is an example of a medical instrument according to the embodiment of the present invention.

The insertion part 14 is configured by sequentially connecting a distal end hard part 18, a bendable part 20, and a soft part 22 from a distal end side toward the proximal end side. FIG. 1 shows a state in which the distal end hard part 18 and the bendable part 20 protrude to the outside from a distal end opening 10A of the guide tube 10.

The distal end hard part 18 is provided with a pair of illumination windows 24 for illuminating an inside of a body and an observation window 26 for acquiring a video of the inside of the body under the illumination from the illumination windows 24. The distal end hard part 18 is provided with a treatment tool lead-out port (not shown) for leading out a treatment tool such as forceps or a high-frequency treatment tool. On the other hand, the bendable part 20 is operated to be bent in a desired direction by operating an angle knob (not shown) provided in the hand operating part 16. The soft part 22 is formed of a flexible member having the flexibility in a bending direction. Since the configuration of the endoscope 12 is well known in the related art, detailed illustration and the description thereof will be omitted here. Hereinafter, the guide tube 10 according to the first embodiment will be described.

Figure 2:
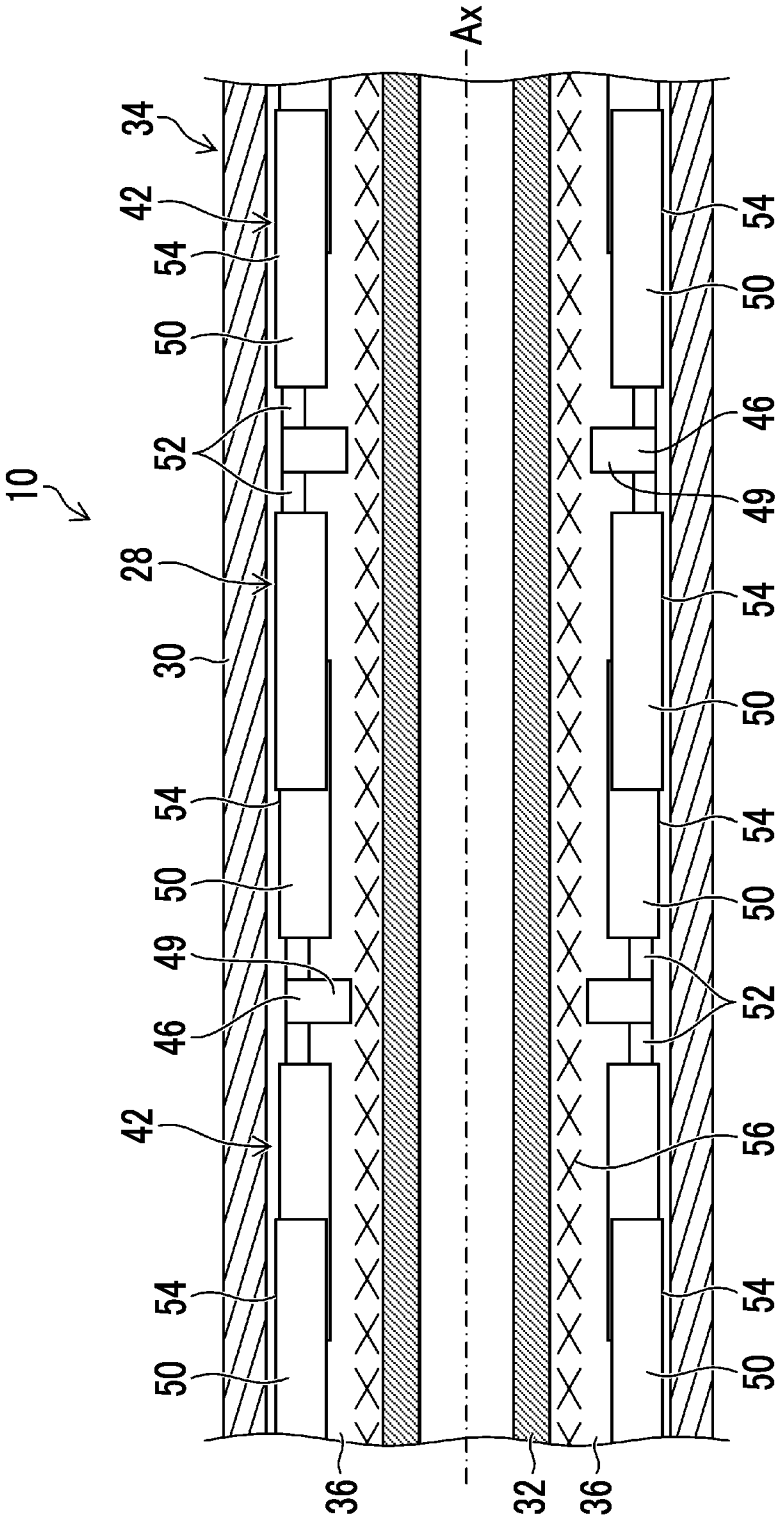
FIG. 2 is an enlarged cross-sectional view of a main part showing a structure of a guide tube of FIG. 1.

FIG. 2 is an enlarged cross-sectional view of a main part showing a structure of the guide tube 10. As shown in FIG. 2, the guide tube 10 includes a tube main body 34 having a double tube structure including an outer tube 30 having the flexibility and an inner tube 32 having the flexibility arranged inside the outer tube 30. Each of the outer tube 30 and the inner tube 32 is made of, for example, a soft resin material which can be bent along a bending part of an intestinal tract. Examples of the soft resin material include urethane or polyester resin, but are not limited thereto. A thickness of each of the outer tube 30 and the inner tube 32 is, for example, about 100 μm, and a thickness of an inner space 36 positioned between the outer tube 30 and the inner tube 32 is, for example, about 800 μm. The thickness of each of the outer tube 30, the inner tube 32, and the inner space 36 is not limited to the above-described thickness, and is set based on a diameter of the insertion part 14 (see FIG. 1), a diameter of an insertion path of a target into which the insertion part 14 is inserted, and the like.

The inner space 36 is a space of which a cross-sectional shape in a direction orthogonal to an axis Ax of the guide tube 10 is formed in an annular shape (donut shape) to surround the periphery (outer periphery) of the inner tube 32, and in which a shape deformable body 28, which will be described later, is arranged. The inner space 36 is formed as a sealed space by sealing the outer tube 30 and the inner tube 32 on the distal end side and the proximal end side of the tube main body 34. As shown in FIG. 1, a pump 38 for supplying and discharging a fluid (for example, air) to and from the inner space 36 is connected to the guide tube 10 via a pipe 40. Here, the pump 38 and the pipe 40 function as a fluid supply and discharge unit according to the embodiment of the present invention.

The shape deformable body 28 is provided between the outer tube 30 and the inner tube 32 (that is, the inner space 36). The shape deformable body 28 is deformable along a shape of the tube main body 34, and includes a plurality of articulated ring members 42 arranged along a direction of the axis Ax of the tube main body 34 as will be described later.

Figure 3:
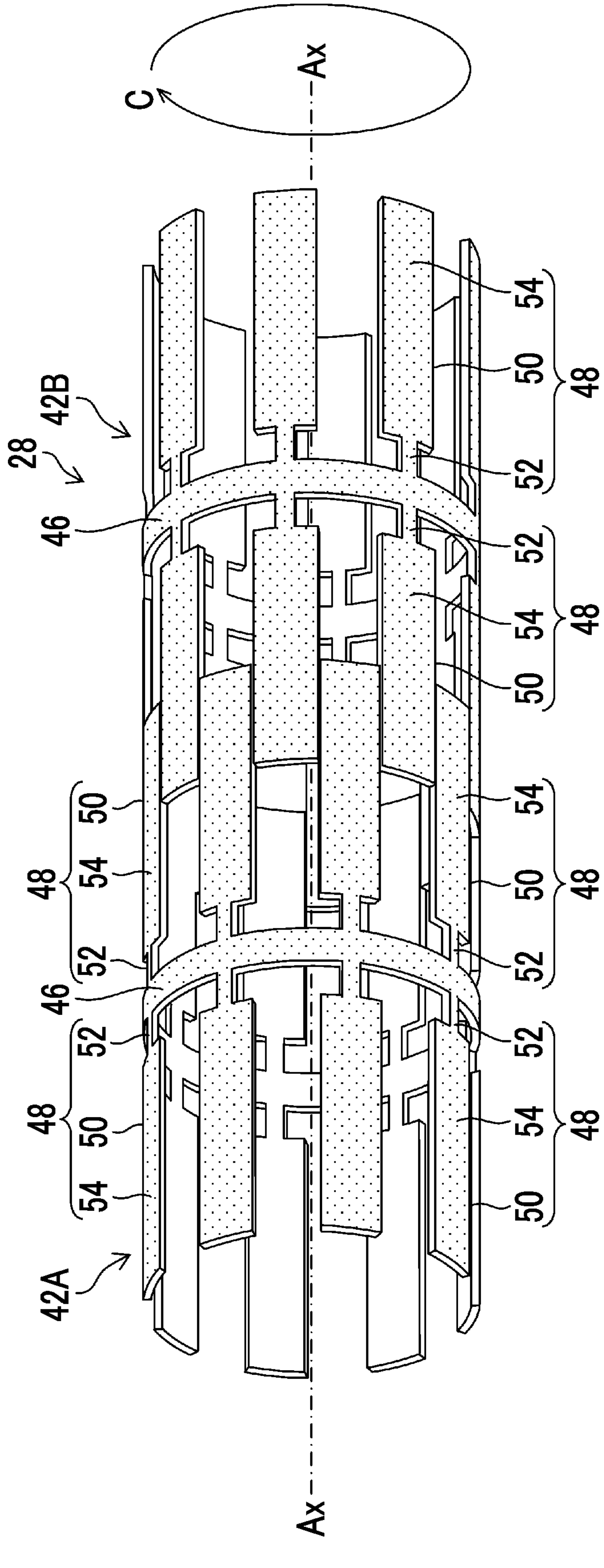
FIG. 3 is a perspective view showing a structure of a shape deformable body provided in the guide tube of FIG. 1.

Hereinafter, the plurality of articulated ring members 42 constituting the shape deformable body 28 will be described in detail with reference to FIG. 3. FIG. 3 is a perspective view showing a structure of the shape deformable body 28 provided in the guide tube 10. FIG. 3 shows two articulated ring members 42A and 42B adjacent to each other in the direction of the axis Ax among the plurality of articulated ring members 42. Here, the articulated ring member 42 corresponds to an articulated ring member according to the embodiment of the present invention. The articulated ring member 42A corresponds to a first articulated ring member according to the embodiment of the present invention, and the articulated ring member 42B corresponds to a second articulated ring member according to the embodiment of the present invention.

The plurality of articulated ring members 42 (see FIG. 2) constituting the shape deformable body 28 are arranged at equal intervals along the direction of the axis Ax of the tube main body 34, and the respective articulated ring members 42 have the same configuration. As shown in FIG. 3, the two articulated ring members 42A and 42B adjacent to each other in the direction of the axis Ax are arranged in a state in which the positions of the articulated ring members 42A and 42B in a circumferential direction C around the direction of the axis Ax are shifted from each other such that articulated pieces 48 described later do not interfere with each other.

The articulated ring member 42 (42A and 42B) includes a fixing ring member 46 that is formed in an annular shape to surround the periphery (outer periphery) of the inner tube 32, and a plurality of articulated pieces 48 extending from the fixing ring member 46 to both sides in the direction of the axis Ax in a comb teeth shape. In the articulated ring member 42, the fixing ring member 46 and the plurality of articulated pieces 48 are integrally made of the same material. The articulated ring member 42 is preferably made of a resin material such as a polypropylene resin, as a constituent material. The articulated ring member 42 may be made of a metal material such as stainless steel.

The fixing ring member 46 is provided such that a relative position thereof in the direction of the axis Ax with respect to the outer tube 30 or the inner tube 32 can be fixed. As shown in FIG. 2, the fixing ring member 46 in the present embodiment includes a fixing piece 49 protruding to the inner tube 32 side, and the fixing piece 49 is fixed to an outer peripheral surface of the inner tube 32 by a fixing unit such as adhesion. As a result, the fixing ring member 46 is fixed at the relative position. A fixing form of the fixing ring member 46 is not limited to the configuration shown in FIG. 2, and may be a form in which the fixing piece 49 protrudes to the outer tube 30 side and is fixed to an inner peripheral surface of the outer tube 30, or may be a form in which the fixing piece 49 protrudes to both the inner tube 32 side and the outer tube 30 side and is fixed to both the inner tube 32 and the outer tube 30.

As shown in FIG. 3, the plurality of articulated pieces 48 extend in a comb teeth shape from the fixing ring member 46 to both sides in the direction of the axis Ax. The respective articulated pieces 48 extending from the fixing ring member 46 to one side are arranged side by side at equal intervals along the circumferential direction C around the direction of the axis Ax in a shape along the shape (annular shape) of the fixing ring member 46.

The articulated piece 48 includes a piece body 50 and a coupling member 52. The piece body 50 50 is formed in an elongated rectangular shape in the direction of the axis Ax. The coupling member 52 couples the piece body 50 and the fixing ring member 46. The coupling member 52 is formed to be narrower than the piece body 50 50, and has a function of smoothly disposing the piece body 50 along the bending direction of the tube main body 34 with respect to the fixing ring member 46 in a case where the tube main body 34 is bent along, for example, the bending part of the intestinal tract.

The articulated ring member 42 includes a high friction surface 54 on a surface (hereinafter, referred to as a "first contact surface") that is in contact with the outer tube 30. Specifically, the high friction surfaces 54 are provided on the first contact surfaces of both the fixing ring member 46 and the articulated piece 48 constituting the articulated ring member 42. Here, in a case where air in the inner space 36 is discharged by the pump 38 (see FIG. 1), the position of the articulated ring member 42 is fixed by the inner peripheral surface of the outer tube 30 being pressed against and closely attached to the articulated ring member 42 and the outer peripheral surface of the inner tube 32 being pressed against and closely attached to the articulated ring member 42. As a result, a state of the tube main body 34 is changed from a flexible state to a high stiffness property state. Then, in this case, the articulated ring member 42 and the outer tube 30 are closely attached to and frictionally engaged with each other via the high friction surface 54. As a result, since the shape (for example, a bent shape) of the shape deformable body 28 is held not to be deformable, a shape holding force of the tube main body 34 in the high stiffness property state (during hardening) is increased. On the contrary, in a case where the air is allowed to flow into the inner space 36 from a state in which the air is discharged, since the shape holding of the shape deformable body 28 is released, the tube main body 34 is changed from the high stiffness property state (hardened state) to the flexible state (non-hardened state or softened state).

Here, the high friction surface described in the present specification refers to a surface having a higher friction coefficient than a contact surface on which the high friction surface is not formed among the contact surfaces. The friction coefficient of the high friction surface can be measured, for example, by the methods described in JISP8147: 2010 or methods based thereon. The high friction surface has a higher friction coefficient than the outer peripheral surface of the outer tube 30 and the inner peripheral surface of the inner tube 32. Further, the term "not to be deformable" described in the present specification means that the shape of the shape deformable body 28 is fixed in a case where the air in the inner space 36 is discharged. Further, the frictional engagement described in the present specification means that the respective contact surfaces are engaged with each other with a frictional force. This frictional force is a frictional force generated in a case where the respective contact surfaces come into contact with each other in a radial direction of the tube main body 34 in a case where the tube main body 34 is viewed from the direction of the axis Ax. Each contact surface is formed in to a substantially circular shape as viewed in the direction of the axis Ax. Hereinafter, a specific example of the high friction surface will be described.

Examples of the high friction surface 54 include a resin layer in which the first contact surface of the articulated ring member 42 is coated with a resin, and as the resin in this case, for example, it is preferable to adopt a resin such as silicone having a high friction coefficient. In addition, examples of the high friction surface 54 include a rough surface formed on the first contact surface, and this rough surface is formed by performing a surface roughening treatment such as blasting, laser irradiation, chemical conversion treatment, or etching on the first contact surface. Further, examples of other aspects of the high friction surface 54 include an aspect in which the resin layer coated on the first contact surface is subjected to surface roughening as well as an aspect in which the rough surface is coated with the resin after the first contact surface is roughened.

In the present embodiment, the surface that is in contact with the inner peripheral surface of the outer tube 30 has been described as an example of the first contact surface of the articulated ring member 42 on which the high friction surface 54 is provided, but the present invention is not limited thereto, and the high friction surface 54 may be provided on a surface (first contact surface) that is in contact with the outer peripheral surface of the inner tube 32. That is, the high friction surface 54 need only be provided on a surface that is in contact with at least one tube of the outer tube 30 or the inner tube 32. For example, even in a case where the high friction surface 54 is provided on the surface that is in contact with the inner tube 32, the frictional force between the articulated ring member 42 and the inner tube 32 is increased, and the shape holding force of the tube main body 34 during hardening can be increased. In addition, the high friction surface 54 may be provided on each surface that is in contact with the outer tube 30 and the inner tube 32. Furthermore, in the present embodiment, as a preferable aspect, the form in which the high friction surface 54 is provided on both the fixing ring member 46 and the articulated piece 48 has been described, but the present invention is not limited thereto, and the high friction surface 54 need only be provided on at least one of the fixing ring member 46 or the articulated piece 48. In a case where the high friction surface 54 is provided on any one of the fixing ring member 46 or the articulated piece 48, an aspect in which the high friction surface 54 is provided on the articulated piece 48 is preferable, and an effect of increasing the shape holding force of the tube main body 34 during hardening can be obtained as compared with an aspect in which the high friction surface 54 is provided on the fixing ring member 46. Further, the high friction surface 54 may be provided on a surface (second contact surface) that is the inner peripheral surface of the outer tube 30 and is in contact with the articulated ring member 42, or may be provided on a surface (second contact surface) that is the outer peripheral surface of the inner tube 32 and is in contact with the articulated ring member 42. Furthermore, the high friction surface 54 may be provided on both the outer tube 30 and the inner tube 32.

Figure 4:
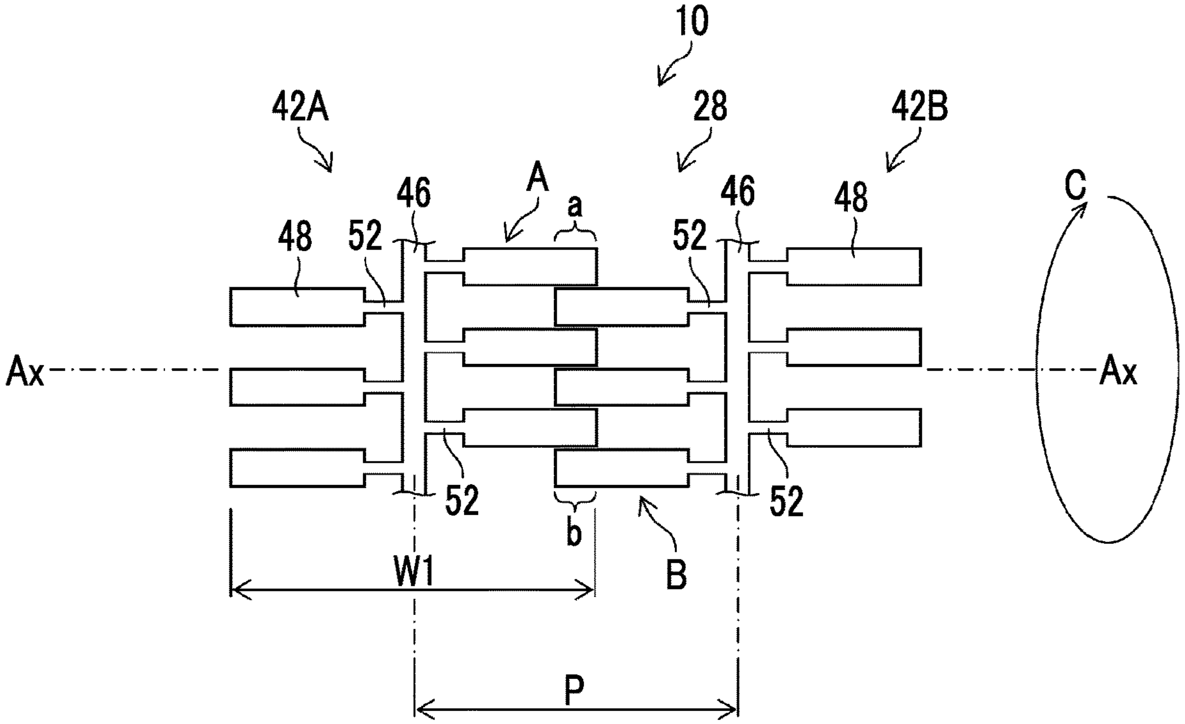
FIG. 4 is an explanatory view schematically showing an arrangement position of an articulated ring member of FIG. 3.

FIG. 4 is an explanatory view schematically showing relative arrangement positions of the articulated ring members 42A and 42B shown in FIG. 3. An example of the arrangement positions of the articulated ring members 42A and 42B shown in FIG. 3 will be described below with reference to FIG. 4.

Here, in order to describe the above-described arrangement positions in an easy-to-understand manner, the description will be made by referring the articulated piece 48 of the articulated ring member 42A extending to the articulated ring member 42B side to as a first articulated piece A, and referring the articulated piece 48 of the articulated ring member 42B extending to the articulated ring member 42A side to as a second articulated piece B. In this case, a first articulated piece end part region a of the first articulated piece A on the articulated ring member 42B side and a second articulated piece end part region b of the second articulated piece B on the articulated ring member 42A side are arranged at positions at which positions thereof in the direction of the axis Ax overlap each other and are arranged at positions at which positions thereof in the circumferential direction C are shifted from each other. That is, in a case in which widths of the articulated ring members 42A and 42B in the direction of the axis Ax are denoted by W1 and arrangement pitches of the articulated ring members 42A and 42B in the direction of the axis Ax are denoted by P, the articulated ring members 42A and 42B are arranged to satisfy $P<W1$. The first articulated pieces A and the second articulated pieces B are alternately arranged one by one along the circumferential direction C.

Figure 5:
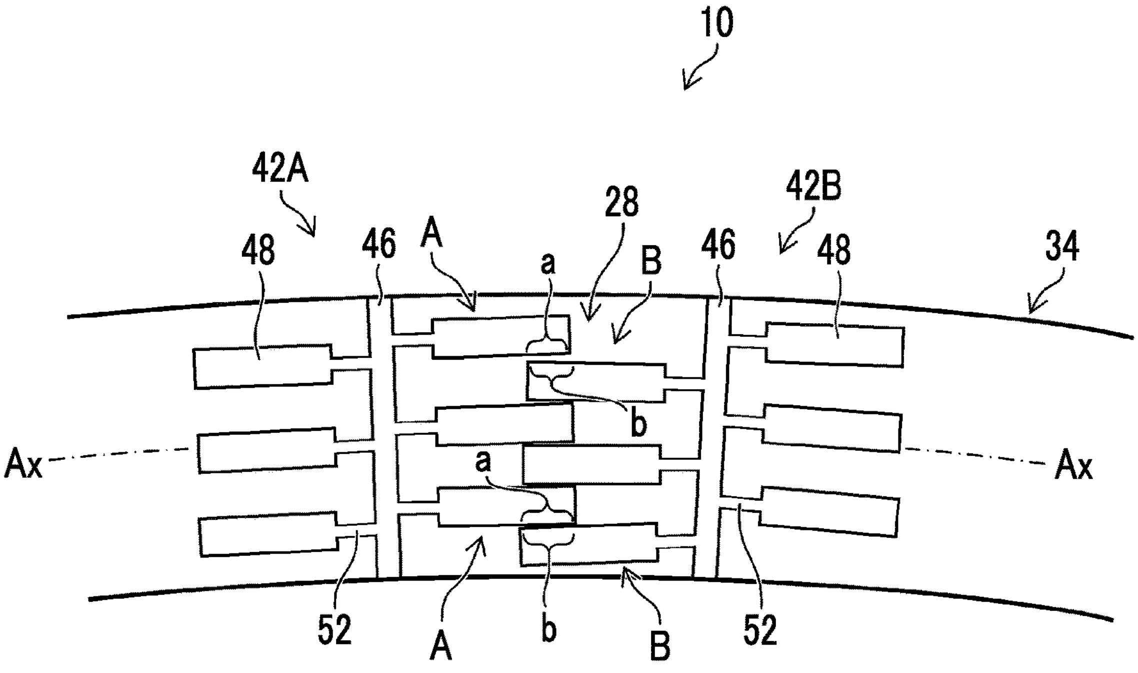
FIG. 5 is a schematic view of a bent tube main body.

With the arrangement positions shown in FIGS. 3 and 4, in a case where the tube main body 34 is bent, the first articulated piece end part region a and the second articulated piece end part region b positioned on an inner peripheral side of the tube main body 34 having a small curvature radius relatively move in a direction of approaching each other, and the first articulated piece end part region a and the second articulated piece end part region b positioned on an outer peripheral side of the tube main body 34 having a large curvature radius relatively move in a direction of separating from each other. Then, as shown in a schematic view of the bent tube main body 34 shown in FIG. 5, the shape deformable body 28 shown in FIG. 3 is deformed into a bent shape along the bent shape of the tube main body 34. In a case where the tube main body 34 is hardened in this state, the tube main body 34 is held in the bent shape which is the shape in this case. Further, as shown in FIG. 3, by arranging the articulated ring member 42A and the articulated ring member 42B along the direction of the axis Ax, the tube main body 34 (in particular, the inner tube 32) is covered with the plurality of articulated ring members 42, so that the tube main body 34 can be hardened without being buckled.

The maximum bent shape of the tube main body 34 is defined by the flexibility of the tube main body 34 itself, a gap between the first articulated piece end part region a and the second articulated piece end part region b in the circumferential direction C, and the like. As a result, the tube main body 34 is bent with the flexibility from a straight rod shape shown in FIG. 1 to the maximum bent shape, and the shape can be held in the bent shape in a case where the tube main body 34 is hardened.

On the other hand, as shown in FIG. 2, the guide tube 10 includes a mesh-like tube (also referred to as a braid or a braided net) 56 in the inner space 36 of the tube main body 34. As an example, the mesh-like tube 56 is arranged in a space between the inner tube 32 and the shape deformable body 28 in the inner space 36, and covers the outer periphery of the inner tube 32. The buckling of the tube main body 34 is also prevented by the mesh-like tube 56. The mesh-like tube 56 is not an essential member in the guide tube 10, but it is preferable to comprise the mesh-like tube 56 from the viewpoint of preventing the buckling.

Next, an example of an operation in a case where the insertion part 14 of the endoscope 12 is guided to a large intestine by using the guide tube 10 will be described with reference to a schematic view of a large intestine 500 shown in FIG. 6.

Figure 6:
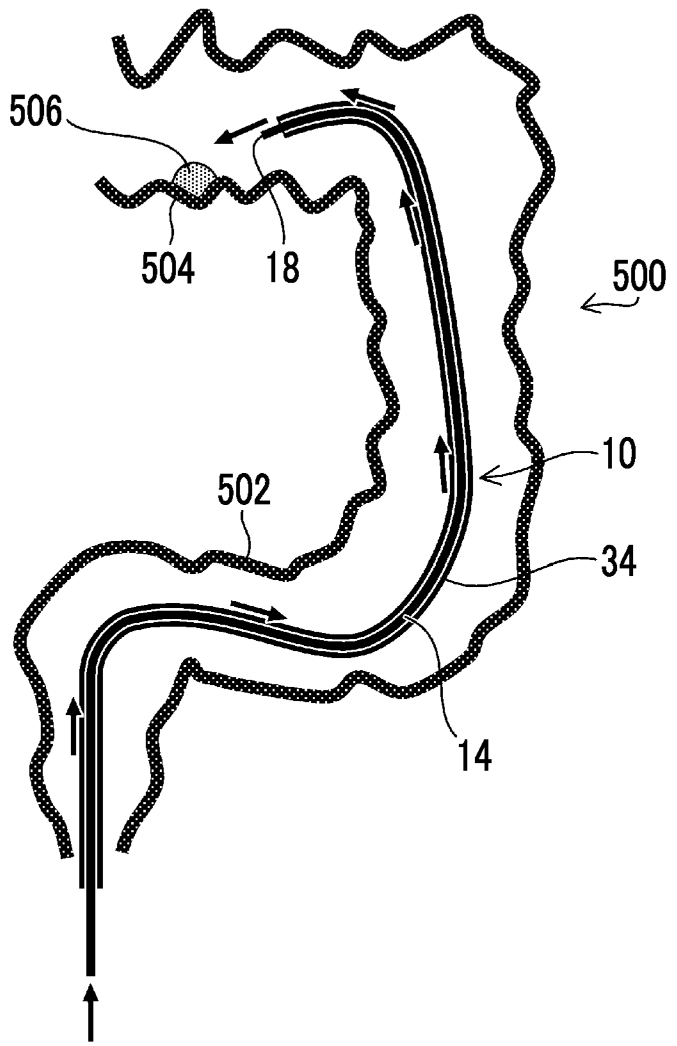
FIG. 6 is an explanatory view of a case where treatment of a lesion portion is performed by using the guide tube.

As shown in FIG. 6, the tube main body 34 of the guide tube 10 is inserted into the large intestine 500 transanally in a state in which the insertion part 14 of the endoscope 12 is inserted. In this case, it is preferable that the endoscope 12 is inserted into the large intestine 500 in a state in which the distal end hard part 18 of the insertion part 14 protrudes forward from the distal end opening 10A (see FIG. 1) of the tube main body 34. As a result, an angle of view forward in an insertion direction can be obtained by the illumination window 24 and the observation window 26 of the distal end hard part 18. The tube main body 34 and the insertion part 14 inserted into the tube main body 34 are inserted along the large intestine 500 while obtaining the angle of view in this manner. In this case, since the insertion part 14 and the tube main body 34 each have the flexibility, the insertion part 14 and the tube main body 34 are smoothly inserted along the bent shape of the large intestine 500.

Here, for example, in a case where a lesion portion 506 of a transverse colon 504 is treated by the endoscope 12 in a state in which the tube main body 34 is disposed along the bent shape of a sigmoid colon (portion not fixed to the body) 502, the pump 38 (see FIG. 1) is operated to suck the air in the inner space 36 from the pipe 40. In this case, the tube main body 34 is deformed into the bent shape along the bent shape of the sigmoid colon 502. As a result, the shape deformable body 28 (see FIG. 3) includes the plurality of articulated ring members 42 is deformed into the bent shape along the bent shape of the tube main body 34 (that is, the bent shape of the sigmoid colon).

Then, in a case where the air in the inner space 36 is sucked as described above, the outer tube 30 and the inner tube 32 of the tube main body 34 are pressed against the plurality of articulated ring members 42 constituting the shape deformable body 28, respectively. As a result, each of the articulated ring members 42 is closely attached to the inner tube 32, and the high friction surface 54 of each of the articulated ring members 42 is closely attached to and frictionally engaged with the outer tube 30. As a result, the tube main body 34 is hardened in a shape corresponding to the bent shape of the sigmoid colon 502, and the shape is held, so that the insertability of the insertion part 14 into the sigmoid colon 502 is improved.

Next, the treatment of the lesion portion 506 of the transverse colon 504 is started by causing the bendable part 20 of the insertion part 14 to protrude forward from the distal end opening 10A of the guide tube 10 and leading out the treatment tool (not shown) forward from the treatment tool lead-out port (not shown) of the distal end hard part 18. In this case, since the insertability of the insertion part 14 into the sigmoid colon 502 is improved by the guide tube 10, the distal end hard part 18 can be positioned at an accurate treatment position, and as a result, it is possible to perform an accurate treatment on the lesion portion 506.

Figure 7:
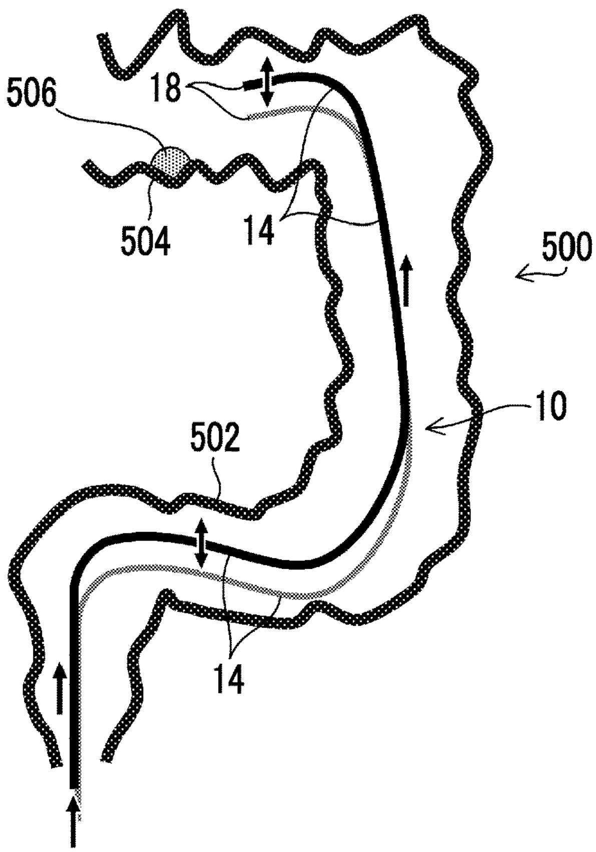
FIG. 7 is an explanatory view of a case where the treatment of the lesion portion is performed only by using an endoscope.

FIG. 7 is a schematic view of a case where the treatment of the lesion portion 506 is performed only by using the endoscope 12 without using the guide tube 10, and is an explanatory view for comparison with the treatment of FIG. 6. According to a treatment method of FIG. 7, since the sigmoid colon 502 is deformed even in a case where the insertion part 14 is pushed into the large intestine 500, it is difficult for the distal end hard part 18 of the insertion part 14 to move forward, and it is also difficult to adjust the position of the distal end hard part 18. As a result, it is difficult to perform an accurate treatment on the lesion portion 506. In contrast, according to a treatment method of FIG. 6 in which the treatment is performed by using the guide tube 10 in combination, since the insertability of the insertion part 14 into the sigmoid colon 502 are improved by the guide tube 10, the distal end hard part 18 is easily moved forward, and the position of the distal end hard part 18 is also easily adjusted. As a result, it is possible to perform an accurate treatment on the lesion portion 506.

As described above, with the guide tube 10 according to the first embodiment, since the shape deformable body 28 includes the plurality of articulated ring members 42 arranged along the direction of the axis Ax of the tube main body 34, each articulated ring member 42 includes the fixing ring member 46 and the plurality of articulated pieces 48, and further the high friction surface 54 is provided on the first contact surface (surface that is in contact with at least one tube of the outer tube 30 or the inner tube 32) of each articulated ring member 42, it is possible to increase the shape holding force of the tube main body 34 while maintaining the flexibility. Accordingly, with the guide tube 10 according to the first embodiment, the insertability of the insertion part 14 of the endoscope 12 can be improved.

Further, since the plurality of articulated pieces 48 of each of the articulated ring members 42 are arranged at equal intervals along the circumferential direction C, a uniform shape holding force can be obtained even in a case where the tube main body 34 is bent in any direction.

In the present embodiment, as one of preferable aspects, the form in which the respective articulated pieces are arranged at equal intervals in the circumferential direction C of each articulated piece 48 has been described, but the present invention is not limited thereto, and the respective articulated pieces may not be arranged at equal intervals in the circumferential direction C of each articulated piece 48. For example, the arrangement interval of the respective articulated pieces 48 in the circumferential direction C may be periodically changed.

Several other embodiments of the guide tube will be described below.

Figure 8:
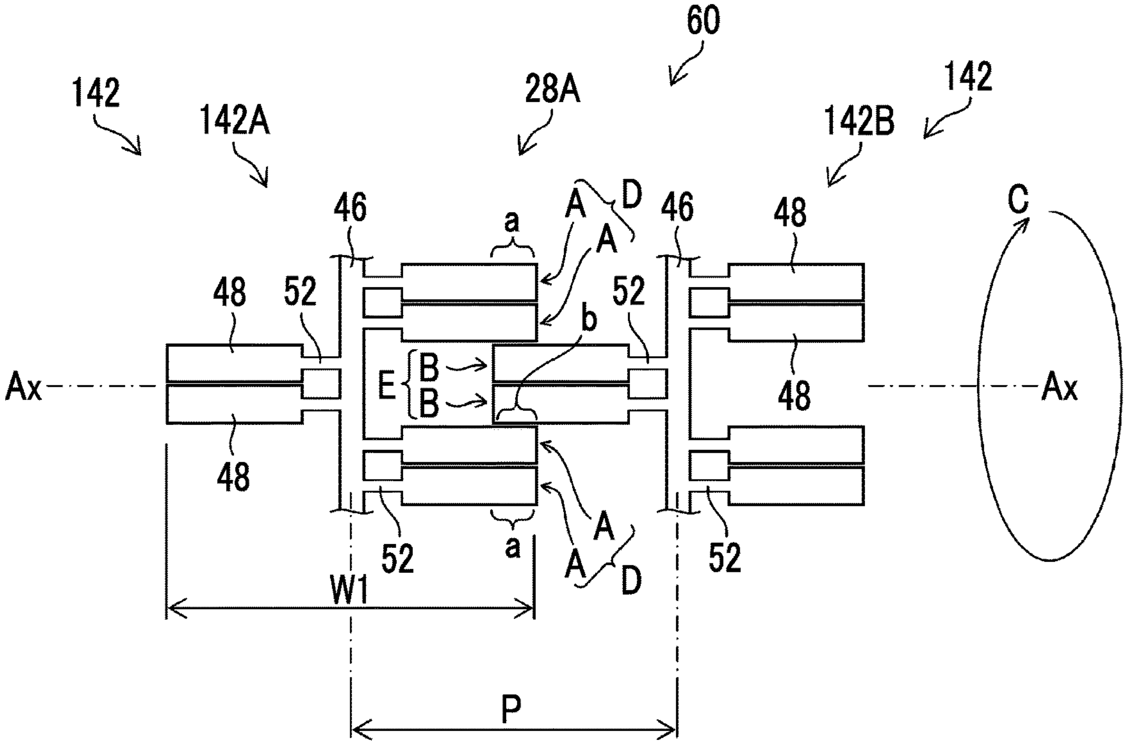
FIG. 8 is an explanatory view schematically showing an arrangement position of an articulated ring member of a guide tube according to a second embodiment.

FIG. 8 is a schematic view showing a configuration of a main part of a shape deformable body 28A provided in a guide tube 60 according to a second embodiment. FIG. 8 schematically shows relative arrangement positions of articulated ring members 142A and 142B adjacent to each other in the direction of the axis Ax among the plurality of articulated ring members 142 arranged along the direction of the axis Ax. The components common to the components in the first embodiment are denoted by the same reference numerals.

Here, a difference between the first embodiment and the second embodiment is that the first articulated pieces A and the second articulated pieces B are alternately arranged one by one along the circumferential direction C in the guide tube 10 according to the first embodiment, whereas a plurality of first articulated piece groups D (two first articulated piece groups D are shown in FIG. 8) consisting of two first articulated pieces A and a plurality of second articulated piece groups E (one second articulated piece group E is shown in FIG. 8) consisting of two second articulated pieces B are alternately arranged along the circumferential direction C in the guide tube 60 of the second embodiment. Since the other configurations are the same, the description thereof will be omitted.

Similarly to the guide tube 10, in the guide tube 60 according to the second embodiment, in a case where the tube main body 34 (see FIG. 2) is bent, the first articulated piece group D and the second articulated piece group E positioned on the inner peripheral side of the tube main body 34 relatively move in a direction of approaching each other, and the first articulated piece group D and the second articulated piece group E positioned on the outer peripheral side of the tube main body 34 relatively move in a direction of separating from each other. Then, by hardening the tube main body 34 in a state in which the tube main body 34 is bent, the tube main body 34 can be held in the bent shape.

Therefore, similarly to the guide tube 10, in the guide tube 60 according to the second embodiment, it is also possible to increase the shape holding force of the tube main body 34 while maintaining the flexibility, so that the insertability of the insertion part 14 of the endoscope 12 can be improved.

In the second embodiment, the aspect in which the first articulated piece group D includes the two first articulated pieces A and the second articulated piece group E includes the two second articulated pieces B has been described, but the present invention is not limited thereto, and the first articulated piece group D and the second articulated piece group E may include three or more first articulated pieces A and three or more second articulated pieces B, respectively. In addition, it is preferable that the first articulated piece group D and the second articulated piece group E are configured respectively at equal intervals in the circumferential direction C. As a result, it is possible to obtain a uniform shape holding force even in a case where the tube main body 34 is bent in any direction.

Figure 9:
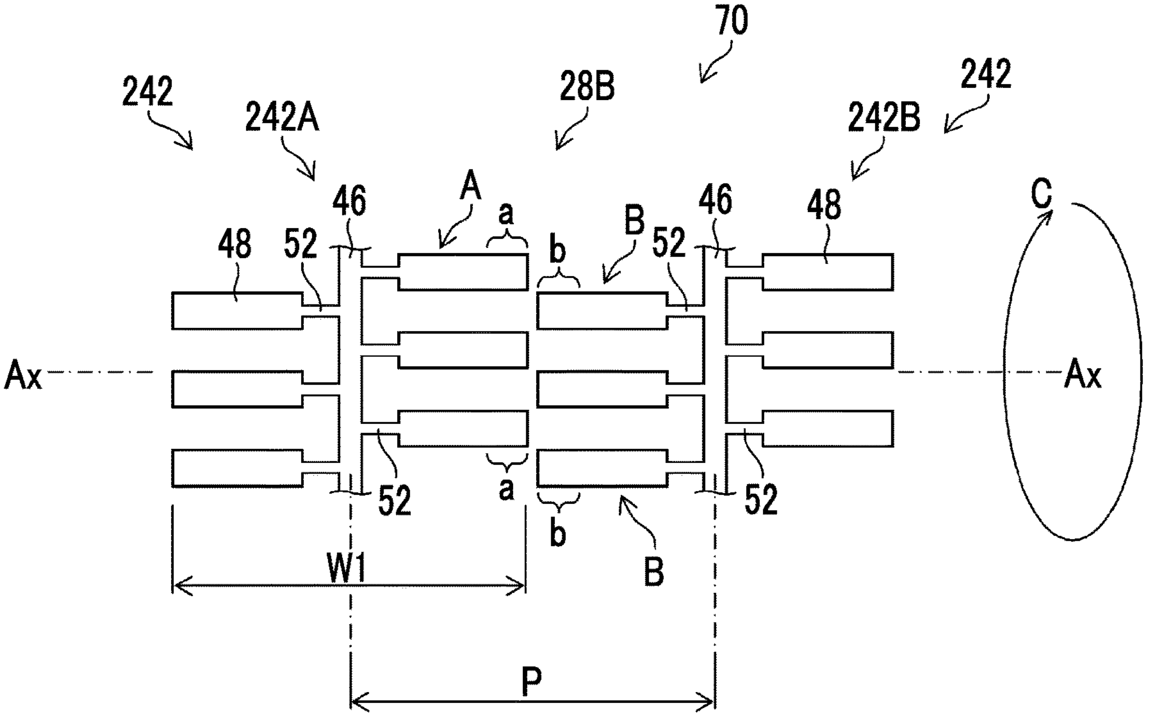
FIG. 9 is an explanatory view schematically showing an arrangement position of an articulated ring member of a guide tube according to a third embodiment.

FIG. 9 is a schematic view showing a configuration of a main part of a shape deformable body 28B provided in a guide tube 70 according to a third embodiment. FIG. 9 schematically shows relative arrangement positions of articulated ring members 242A and 242B adjacent to each other in the direction of the axis Ax among the plurality of articulated ring members 242 arranged along the direction of the axis Ax. The components common to the components in the first embodiment are denoted by the same reference numerals.

Here, a difference between the first embodiment and the third embodiment is that the positions of the first articulated piece end part region a and the second articulated piece end part region b in the direction of the axis Ax are arranged respectively at positions overlapping each other in the guide tube 10 according to the first embodiment, whereas the positions of the first articulated piece A and the second articulated piece B in the direction of the axis Ax are arranged respectively at positions shifted from each other in the guide tube 70 according to the third embodiment. That is, in a case in which widths of the articulated ring members 242A and 242B of the guide tube 70 in the direction of the axis Ax are denoted by W1 and arrangement pitches of the articulated ring members 242A and 242B in the direction of the axis Ax are denoted by P, the articulated ring members 242A and 242B are arranged to satisfy $P>W1$. It should be noted that the articulated ring members 242A and 242B may be arranged to satisfy $P=W1$. Since the other configurations are the same, the description thereof will be omitted.

Similarly to the guide tube 10, in the guide tube 70 according to the third embodiment, in a case where the tube main body 34 (see FIG. 2) is bent, the first articulated piece end part region a and the second articulated piece end part region b positioned on the inner peripheral side of the tube main body 34 relatively move in a direction of approaching each other, and the first articulated piece end part region a and the second articulated piece end part region b positioned on the outer peripheral side of the tube main body 34 relatively move in a direction of separating from each other.

Then, by hardening the tube main body 34 in a state in which the tube main body 34 is bent, the tube main body 34 can be held in the bent shape.

Therefore, similarly to the guide tube 10, in the guide tube 70 according to the third embodiment, it is also possible to increase the shape holding force of the tube main body 34 while maintaining the flexibility, so that the insertability of the insertion part 14 of the endoscope 12 can be improved.

Figure 10:
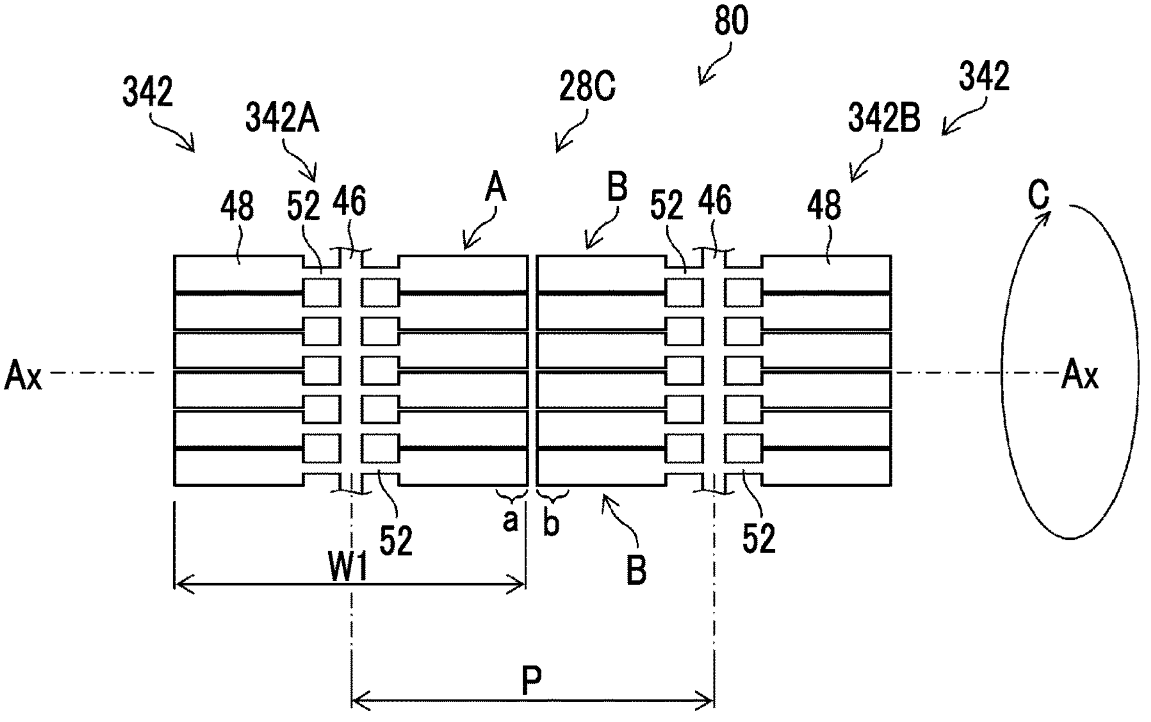
FIG. 10 is an explanatory view schematically showing an arrangement position of an articulated ring member of a guide tube according to a fourth embodiment.

FIG. 10 is a schematic view showing a configuration of a main part of a shape deformable body 28C provided in a guide tube 80 according to a fourth embodiment. FIG. 10 schematically shows relative arrangement positions of articulated ring members 342A and 342B adjacent to each other in the direction of the axis Ax among the plurality of articulated ring members 342 arranged along the direction of the axis Ax. The components common to the components in the third embodiment are denoted by the same reference numerals.

Here, a difference between the third embodiment and the fourth embodiment is that the respective intervals between the plurality of first articulated pieces A and the plurality of second articulated pieces B in the circumferential direction C are wide in the guide tube 70 according to the third embodiment, whereas the respective intervals between the plurality of first articulated pieces A and the plurality of second articulated pieces B in the circumferential direction C are narrow, and the positions of the first articulated piece end part region a and the second articulated piece end part region b in the circumferential direction C are arranged at positions overlapping each other in the guide tube 80 of the fourth embodiment. Since the other configurations are the same, the description thereof will be omitted.

Similarly to the guide tube 70, in the guide tube 80 according to the fourth embodiment configured in this way, it is also possible to improve the shape holding force of the tube main body 34 while maintaining the flexibility, so that the insertability of the insertion part 14 of the endoscope 12 can be improved.

Figure 11:
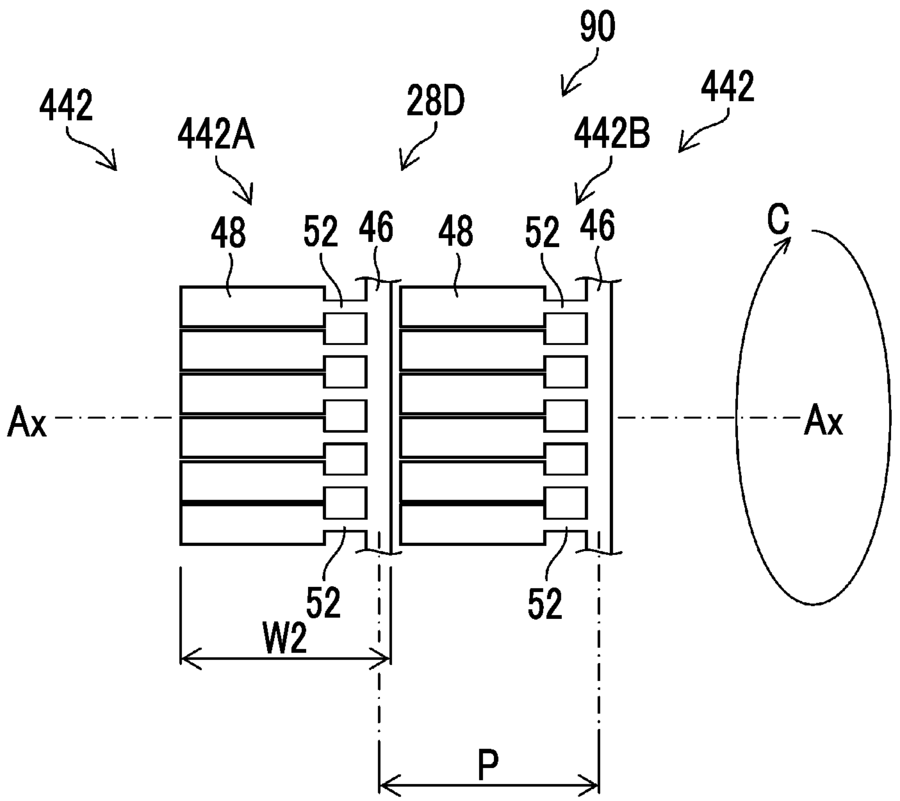
FIG. 11 is an explanatory view schematically showing an arrangement position of an articulated ring member of a guide tube according to a fifth embodiment.

FIG. 11 is a schematic view showing a configuration of a main part of a shape deformable body 28D provided in a guide tube 90 according to a fifth embodiment. FIG. 11 schematically shows relative arrangement positions of articulated ring members 442A and 442B adjacent to each other in the direction of the axis Ax among the plurality of articulated ring members 442 arranged along the direction of the axis Ax. The components common to the components in the fourth embodiment are denoted by the same reference numerals.

Here, a difference between the fourth embodiment and the fifth embodiment is that the plurality of articulated pieces 48 extend from the fixing ring member 46 to both sides in the direction of the axis Ax in the guide tube 80 according to the fourth embodiment, whereas the plurality of articulated pieces 48 of each of the articulated ring members 442A and 442B extend from the fixing ring member 46 to only one side (the left side in FIG. 11) in the direction of the axis Ax in the guide tube 90 according to the fifth embodiment. Since the other configurations are the same, the description thereof will be omitted. Although, a width (W2) of the guide tube 90 is smaller than the width (W1) of the guide tube 90 in a case of the guide tube 80 in which the articulated pieces 48 extend to both sides, the arrangement satisfies P>W2 similarly to the guide tube 80.

With the guide tube 90 according to the fifth embodiment, in a case where the tube main body 34 (see FIG. 2) is bent, the fixing ring member 46 of the articulated ring member 442A positioned on the inner peripheral side of the tube main body 34 and the articulated piece 48 of the articulated ring member 442B relatively move in a direction of approaching each other, and the fixing ring member 46 of the articulated ring member 442A positioned on the outer peripheral side of the tube main body 34 and the articulated piece 48 of the articulated ring member 442B relatively move in a direction of separating from each other. Then, by hardening the tube main body 34 in a state in which the tube main body 34 is bent, the tube main body 34 can be held in the bent shape.

Therefore, similarly to the guide tube 80, in the guide tube 90 according to the fifth embodiment, it is also possible to increase the shape holding force of the tube main body 34 while maintaining the flexibility, so that the insertability of the insertion part 14 of the endoscope 12 can be improved.

Figure 12:
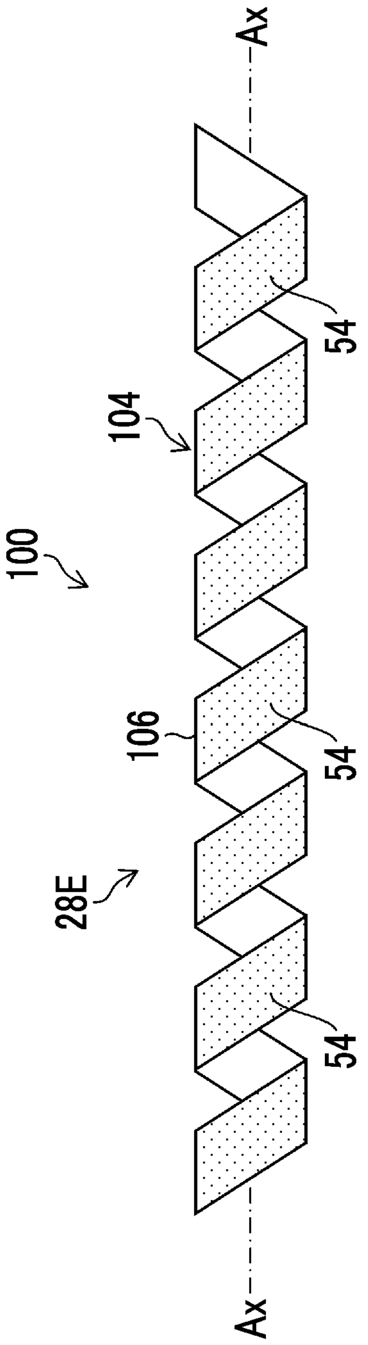
FIG. 12 is a structural view of a spiral tube adopted in a guide tube according to a sixth embodiment.

FIG. 12 is a schematic view showing a configuration of a main part of a shape deformable body 28E provided in a guide tube 100 according to a sixth embodiment.

A difference between the first to fifth embodiments and the sixth embodiment is that the articulated ring members 42, 142, 242, 342, and 442 are adopted as the shape deformable bodies 28, and 28A to 28D in the guide tubes 10, 60, 70, 80, and 90 according to the first to fifth embodiments, whereas a spiral tube 104 is adopted as the shape deformable body 28E in the guide tube 100 according to the sixth embodiment. Since the other configurations are the same, the description thereof will be omitted.

Figure 13:
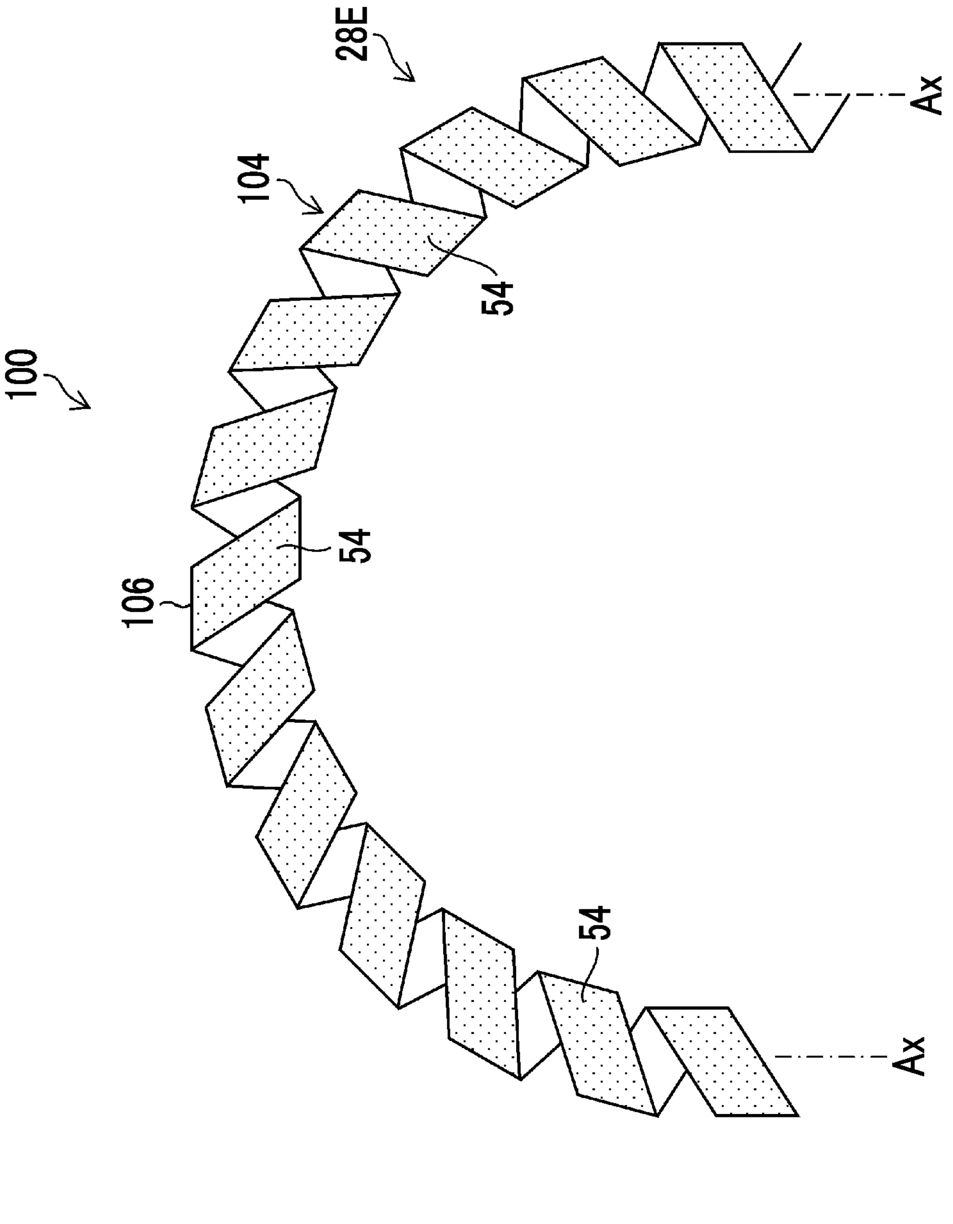
FIG. 13 is an explanatory view in which the spiral tube is deformed into a bent shape.

The spiral tube 104 is formed by spirally winding a band-shaped member 106 and is provided on the outer peripheral side of the inner tube (see FIG. 2). Further, the spiral tube 104 includes the high friction surface 54 on the surface (first contact surface) that is in contact with at least one tube (outer tube 30 in FIG. 12) of the outer tube 30 or the inner tube 32 shown in FIG. 2. Accordingly, in a case where the air in the inner space 36 is discharged by the pump 38 (see FIG. 1), the spiral tube 104 and the outer tube 30 of the tube main body 34 (see FIG. 2) of the guide tube 100 are closely attached to and frictionally engaged with each other via the high friction surface 54. As a result, since the shape of the spiral tube 104 is held not to be deformable, the shape holding force of the tube main body 34 in the high stiffness property state (during hardening) is increased. In addition, since the spiral tube 104 has the flexibility in the bending direction, the shape thereof is deformable into, for example, the bent shape as shown in FIG. 13.

Next, an example of an operation in a case where the insertion part 14 of the endoscope 12 is guided to the large intestine 500 (see FIG. 6) by using the guide tube 100 will be described.

First, since the insertion part 14, the tube main body 34, and the spiral tube 104 each have the flexibility, in a case where the tube main body 34 and the insertion part 14 inserted into the tube main body 34 are inserted along the large intestine 500, the insertion part 14 is smoothly inserted along the bent shape of the large intestine 500.

Next, in a case where the pump 38 is operated in a state in which the tube main body 34 is disposed along the bent shape of the sigmoid colon 502 to suck the air in the inner space 36 from the pipe 40, the outer tube 30 and the inner tube 32 are pressed against the spiral tube 104. As a result, the spiral tube 104 is closely attached to the inner tube 32, and the high friction surface 54 of the spiral tube 104 is closely attached to and frictionally engaged with the outer tube 30. As a result, the tube main body 34 is hardened in a shape corresponding to the bent shape of the sigmoid colon 502, and the shape is held, so that the insertability of the insertion part 14 into the sigmoid colon 502 is improved.

Next, the treatment of the lesion portion 506 of the transverse colon 504 is started by causing the bendable part 20 of the insertion part 14 to protrude forward from the distal end opening 10A of the guide tube 100 and leading out the treatment tool (not shown) forward from the treatment tool lead-out port (not shown) of the distal end hard part 18. In this case, since the insertability of the insertion part 14 into the sigmoid colon 502 is improved by the guide tube 100, the distal end hard part 18 can be positioned at an accurate treatment position, and as a result, it is possible to perform an accurate treatment on the lesion portion 506.

As described above, with the guide tube 100 according to the sixth embodiment, since the shape deformable body 102 includes the spiral tube 104 and the spiral tube 104 includes the high friction surface 54, it is possible to increase the shape holding force of the tube main body 34 while maintaining the flexibility. Accordingly, with the guide tube 100 according to the sixth embodiment, the insertability of the insertion part 14 of the endoscope 12 can be improved. Even in the sixth embodiment, the high friction surface 54 may be provided on the surface of the spiral tube 104 that is in contact with the inner tube 32, or the high friction surface 54 may be provided on at least one tube of the outer tube 30 or the inner tube 32.

Figure 14:
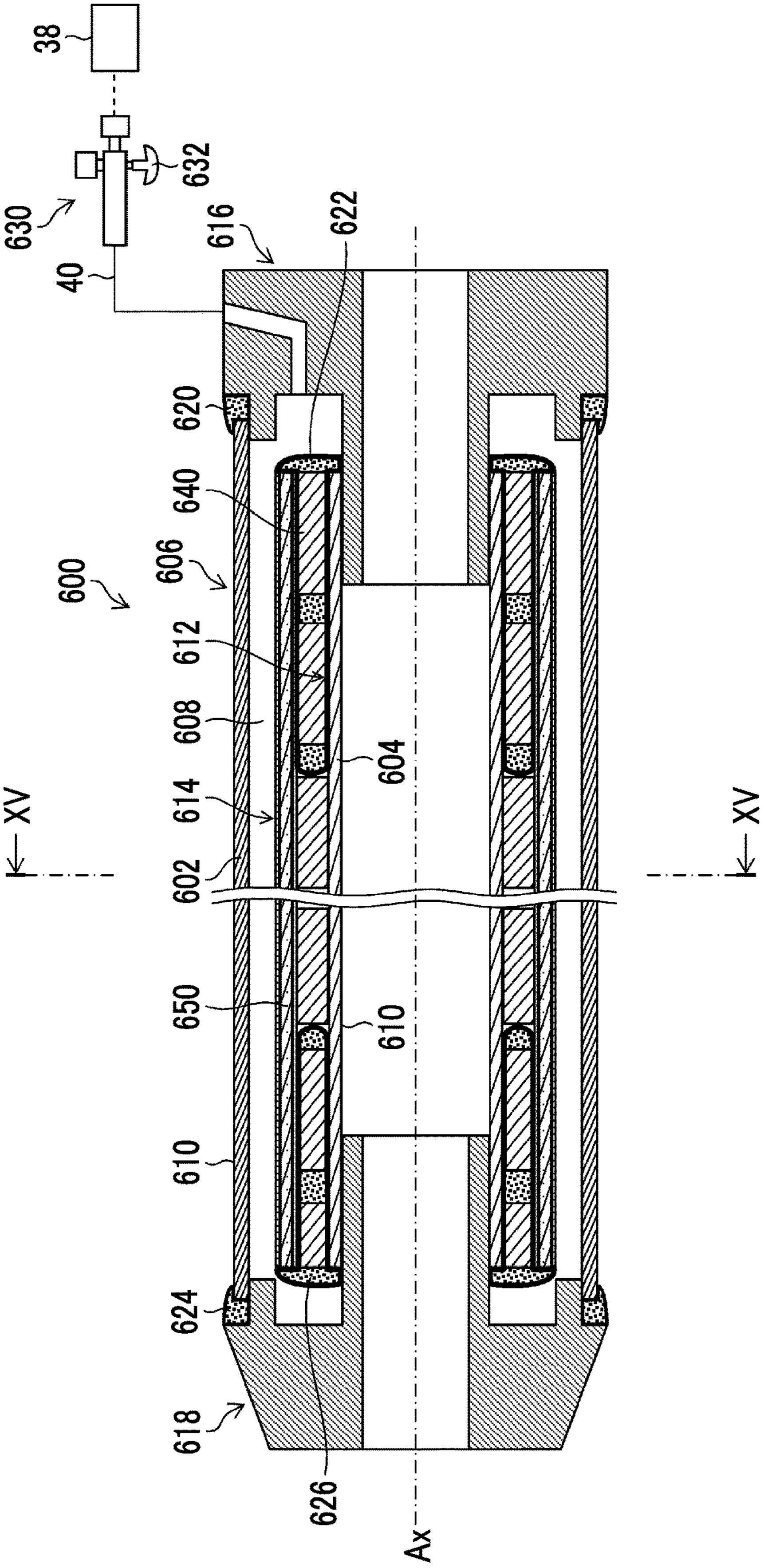
FIG. 14 is an enlarged cross-sectional view showing a structure of a guide tube according to a seventh embodiment.
Figure 15:
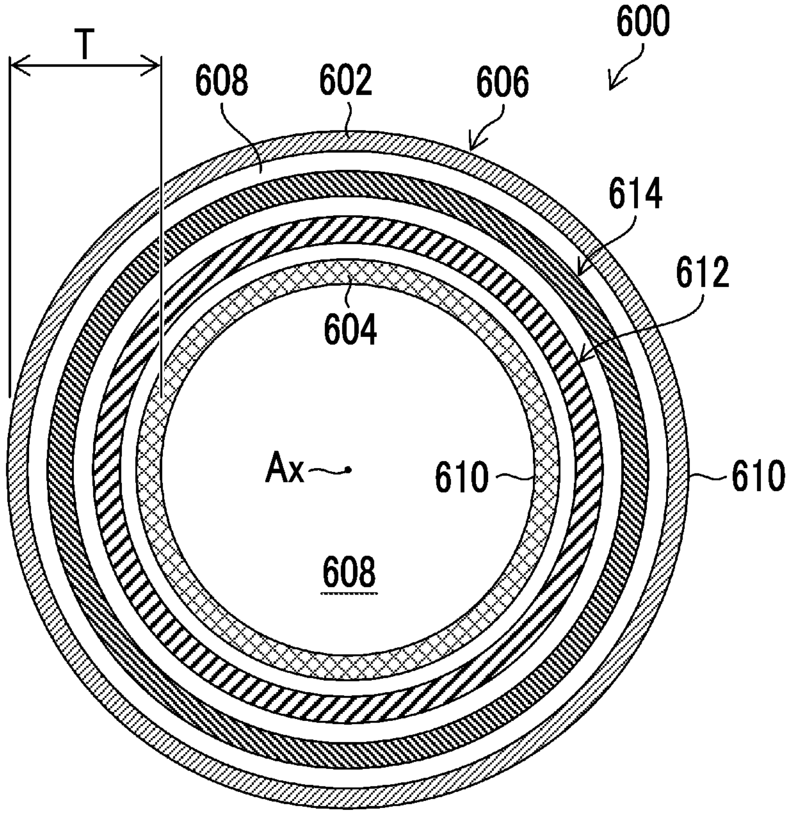
FIG. 15 is a vertical cross-sectional view of the guide tube taken along a line XV-XV of FIG. 14.

FIG. 14 is an enlarged cross-sectional view showing a structure of a guide tube 600 according to a seventh embodiment. In FIG. 14, a part of the guide tube 600 in the direction of the axis Ax is shown in a cutaway manner. FIG. 15 is a schematic cross-sectional view of the guide tube 600 taken along a line XV-XV in FIG. 14. The components common to the components of the guide tube 10 according to the first embodiment are denoted by the same reference numerals.

As shown in FIGS. 14 and 15, the guide tube 600 includes a tube main body 606 having a double tube structure including an outer tube 602 having flexibility and an inner tube 604 having flexibility arranged inside the outer tube 602. Each of the outer tube 602 and the inner tube 604 is made of, for example, a soft resin material which can be bent along the bending part of the intestinal tract. Examples of the soft resin material include urethane (polyurethane resin). However, the present invention is not limited thereto, and for example, as the outer tube 602 and the inner tube 604, any material can be applied as long as the material has an elastic modulus of about 5 to 20 MPa at an elongation rate of 100%, which is obtained by the methods described in JISK7161 (tensile test) or methods based thereon. A thickness of each of the outer tube 602 and the inner tube 604 is, for example, about 100 μm to 200 μm, and a total thickness of the outer tube 602 and the inner tube 604 is about 200 μm to 400 μm. From the viewpoint of preventing breakage, the thickness of the outer tube 602 is preferably larger than the thickness of the inner tube 604.

A thickness of an inner space 608 positioned between the outer tube 602 and the inner tube 604 is about 600 μm to 800 μm, for example, in a case where a thickness T of the tube main body 606 shown in FIG. 15 is about 1 mm (for example, 1 mm at maximum). The thickness of each of the outer tube 602, the inner tube 604, and the inner space 608 is not limited to the above-described thickness, and is set based on the diameter of the insertion part 14 (see FIG. 1), the diameter of the insertion path of the target into which the insertion part 14 is inserted, and the like. Further, an inner diameter of the inner tube 604 is also set based on the diameter of the insertion part 14, and the inner diameter is, for example, about 6 mm to 16 mm.

An outer peripheral surface of the outer tube 602 and an inner peripheral surface of the inner tube 604 each include a hydrophilic coating 610. By forming the hydrophilic coating 610 on the outer peripheral surface of the outer tube 602, a frictional resistance between the outer tube 602 and the large intestine 500 (see FIG. 6) can be reduced. As a result, the insertability (forward mobility) of the tube main body 606 into the large intestine 500 is improved. Further, by forming the hydrophilic coating 610 on the inner peripheral surface of the inner tube 604, it is possible to reduce a frictional resistance between the inner tube 604 and the insertion part 14 (see FIG. 1). As a result, the insertability of the insertion part 14 into the tube main body 606 is improved. It should be noted that, in the present example, the form in which the hydrophilic coating 610 is formed on both the outer tube 602 and the inner tube 604 has been described as an example, but the present invention is not limited thereto, and the hydrophilic coating 610 may be formed on at least one of the outer tube 602 or the inner tube 604. However, it is preferable to form the hydrophilic coating 610 on both the outer tube 602 and the inner tube 604 because the above-described two effects can be obtained together.

The inner space 608 is a space of which a cross-sectional shape in the direction orthogonal to the axis Ax of the guide tube 600 is formed in an annular shape (donut shape) to surround the periphery (outer periphery) of the inner tube 604, and in which a shape deformable body 612 and an interlayer 614, which will be described later, are arranged.

As shown in FIG. 14, caps 616 and 618 having a ring shape are adhered to a proximal end side and a distal end side of the tube main body 606, respectively, and the outer tube 602 and the inner tube 604 are sealed by the caps 616 and 618. As a result, the inner space 608 is formed as the sealed space. The pump 38 for supplying and discharging a fluid (for example, air) to and from the inner space 608 is connected to the cap 616 on the proximal end side of the tube main body 606 via the pipe 40.

Figure 16:
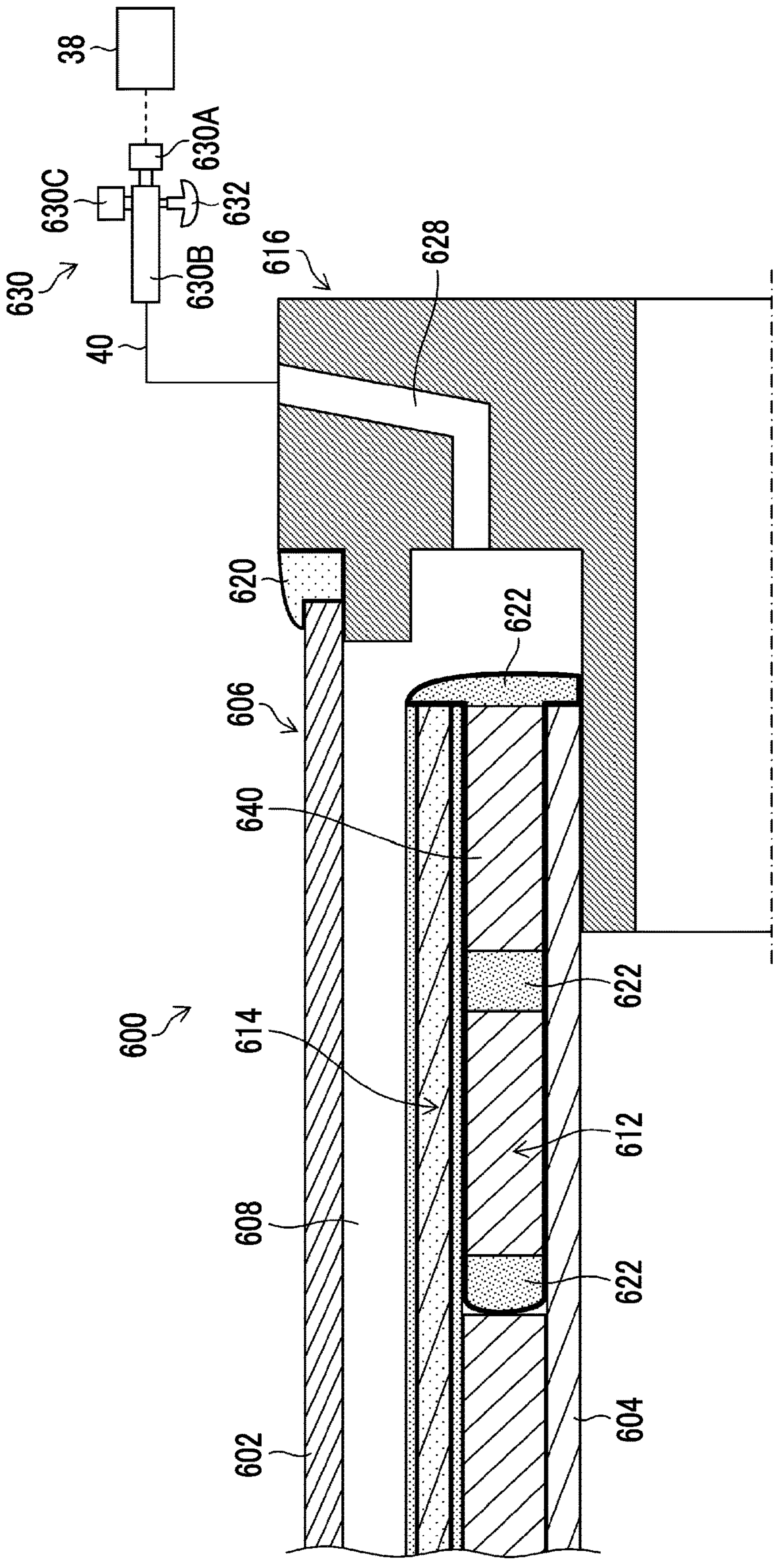
FIG. 16 is an enlarged cross-sectional view of a main part on a proximal end side of the guide tube shown in FIG. 14.

FIG. 16 is an enlarged cross-sectional view of a main part on the proximal end side of the guide tube 600 shown in FIG. 14. As shown in FIG. 16, the cap 616 on the proximal end side of the tube main body 606 is adhered to the proximal end side of the outer tube 602 via an adhesive 620 and is adhered to the proximal end side of the inner tube 604 via an adhesive 622. The proximal end side of each of the shape deformable body 612 and the interlayer 614 is adhered to the cap 616 by the adhesive 622.

Figure 17:
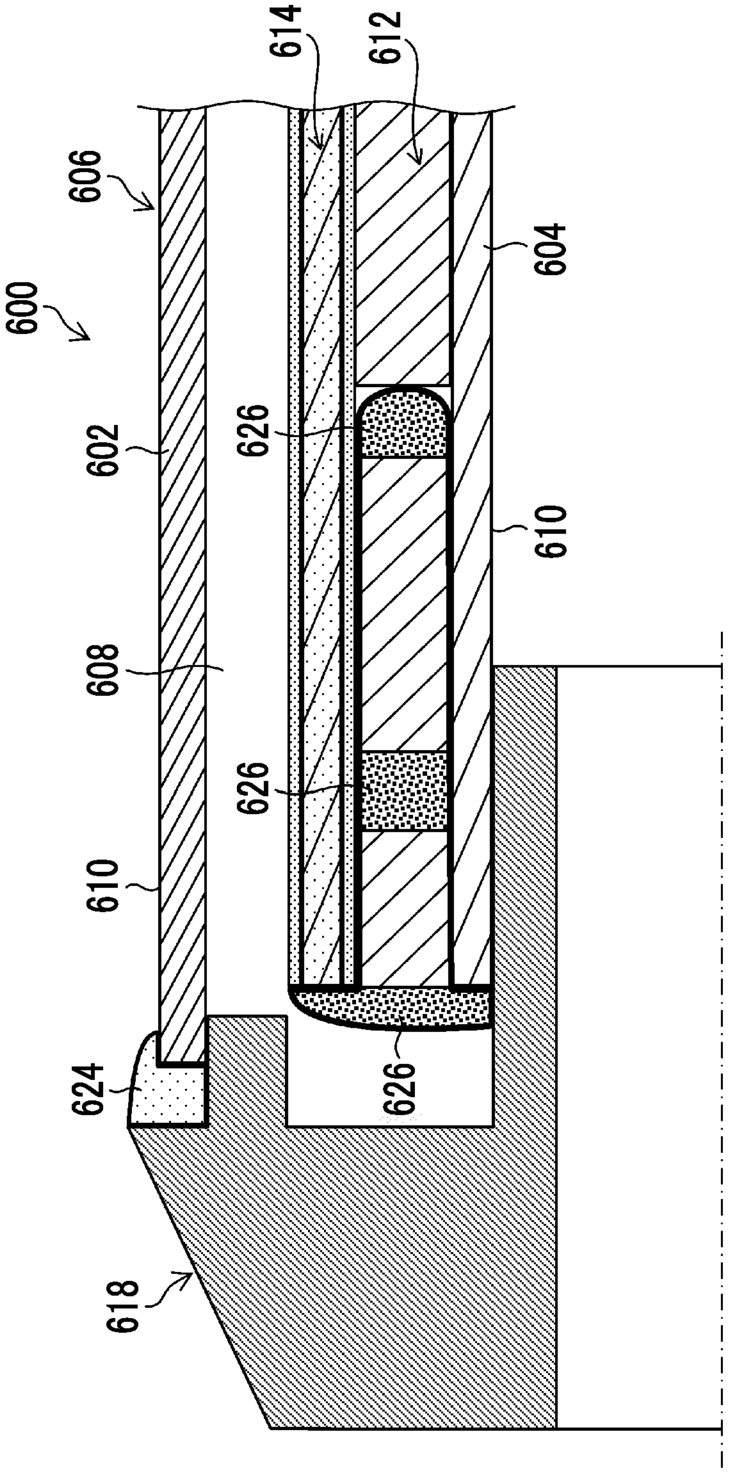
FIG. 17 is an enlarged cross-sectional view of a main part on a distal end side of the guide tube shown in FIG. 14.

FIG. 17 is an enlarged cross-sectional view of a main part on the distal end side of the guide tube 600 shown in FIG. 14. As shown in FIG. 17, the cap 618 on the distal end side of the tube main body 606 is adhered to the distal end side of the outer tube 602 via an adhesive 624 and is adhered to the distal end side of the inner tube 604 via an adhesive 626. The distal end side of each of the shape deformable body 612 and the interlayer 614 is adhered to the cap 618 by the adhesive 626.

Returning to FIG. 16, the cap 616 on the proximal end side includes a ventilation hole 628 that allows the inner space 608 and the pipe 40 to communicate with each other. The pipe 40 is connected to the pump 38 via a three way stopcock 630. The three way stopcock 630 includes a first port 630A connected to the pump 38, a second port 630B connected to the pipe 40, and a third port 630C open to the atmosphere. Further, the three way stopcock 630 includes a cock 632 which is an example of a switching member according to the embodiment of the present invention. By operating the cock 632, an operator can selectively switch between an ON mode in which the first port 630A and the second port 630B communicate with each other and an OFF mode in which the first port 630A and the third port 630C communicate with each other. In a case where the cock 632 is switched to the ON mode, the pump 38 and the inner space 608 communicate with each other. As a result, air in the inner space 608 is sucked by the pump 38 and is opened to the atmosphere, or the air (atmosphere) is supplied to (flows into) the inner space 608 by the pump 38. In a case where the cock 632 is switched to the OFF mode, the pump 38 and outside air communicate with each other. As a result, the supply and discharge of the air to and from the inner space 608 are stopped. The above-described switching operation using the three way stopcock 630 is an operation performed in a state in which the pump 38 is regularly operated, but the above-described switching operation can also be performed by starting (ON) and stopping (OFF) the pump 38 instead of this operation. In this case, the ON and OFF operations of the pump 38 can be performed by a foot switch (not shown) which is another example of the switching member according to the embodiment of the present invention. Further, an operation button (not shown) for performing the ON and OFF operations of the pump 38 may be provided in the hand operating part 16 of the endoscope 12 (see FIG. 1). The operation button is an example of a switching unit according to the embodiment of the present invention.

Next, the shape deformable body 612 shown in FIGS. 14 and 15 will be described. The shape deformable body 612 is provided between the outer tube 602 and the inner tube 604 (that is, the inner space 608). The shape deformable body 612 is deformable along the shape of the tube main body 606, and includes a spiral tube 640 arranged along the direction of the axis Ax of the tube main body 606.

Figure 18:
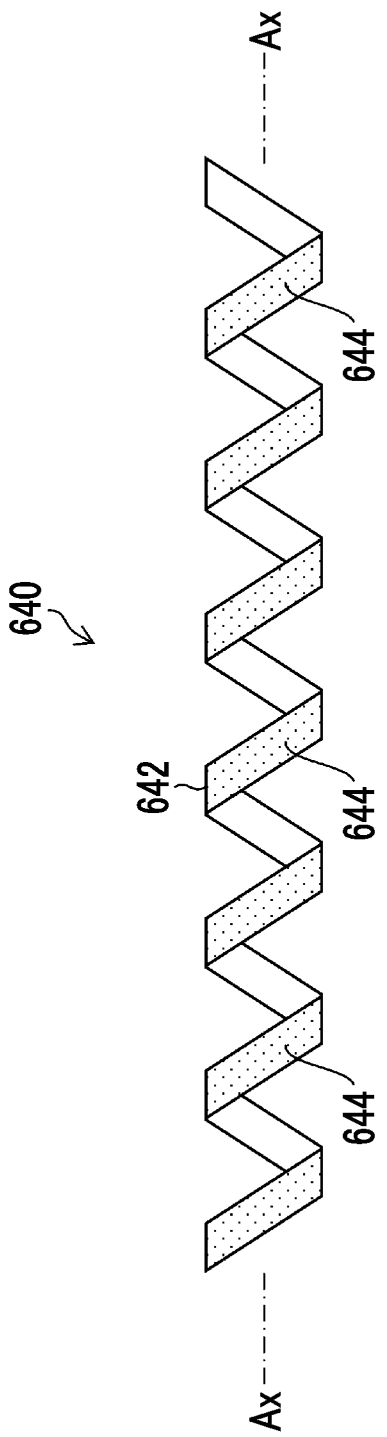
FIG. 18 is an external view of the spiral tube.
Figure 19:
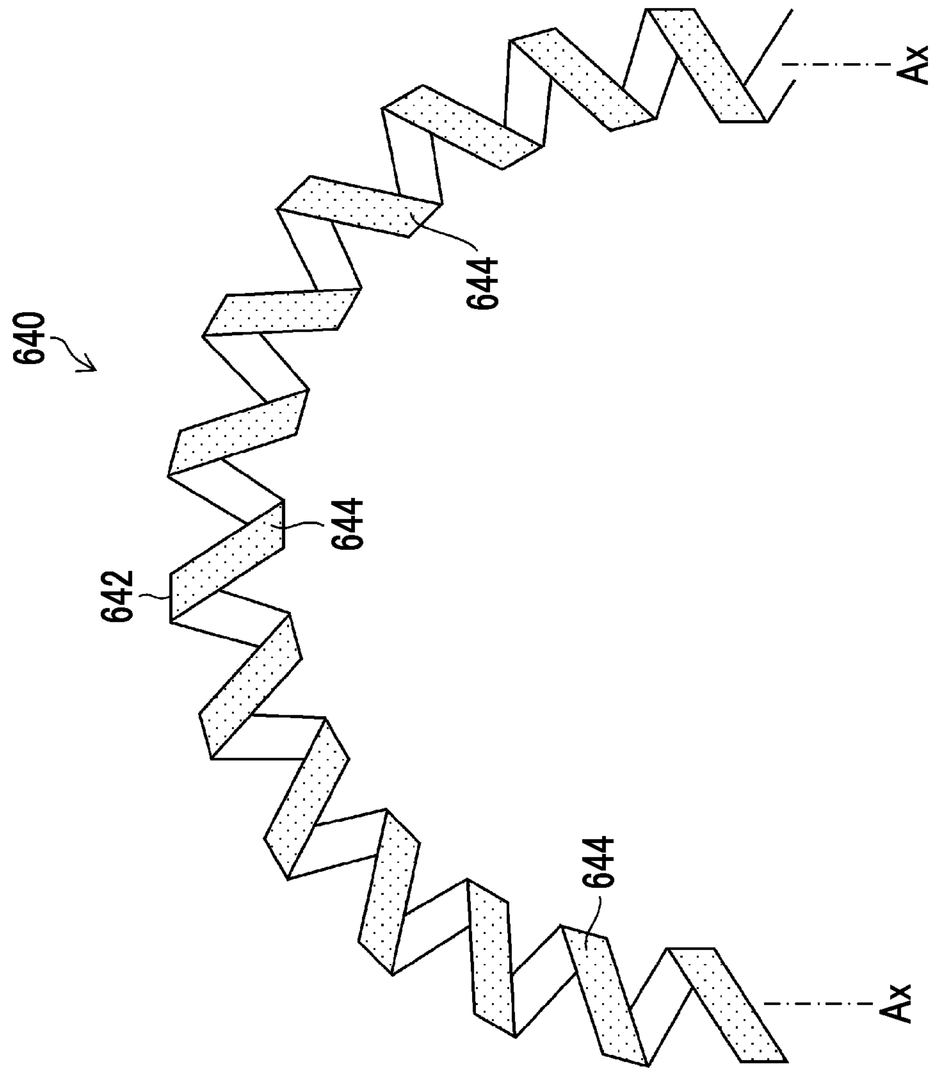
FIG. 19 is an explanatory view in which the spiral tube shown in FIG. 18 is deformed into a bent shape.

FIG. 18 is an external view of the spiral tube 640. As shown in FIG. 18, the spiral tube 640 is formed by spirally winding a band-shaped member 642 and is provided on an outer peripheral side of the inner tube 604 (see FIG. 14). In addition, the spiral tube 640 includes a high friction surface 644 on a surface (outer peripheral surface and first contact surface) which is in contact with the interlayer 614 (see FIG. 14) which will be described later. Accordingly, in a case where the air in the inner space 608 (see FIG. 14) is discharged by the pump 38 (see FIG. 14), the spiral tube 640 and the interlayer 614 of the tube main body 606 (see FIG. 14) are closely attached to and frictionally engaged with each other via the high friction surface 644. As a result, since the shape (for example, a bent shape) of the spiral tube 640 is held not to be deformable, a shape holding force of the tube main body 606 in the high stiffness property state (during hardening) is increased. In addition, since the spiral tube 640 has the flexibility in the bending direction, the shape thereof is deformable into, for example, the bent shape as shown in FIG. 19.

The band-shaped member 642 of the spiral tube 640 is made of, for example, stainless steel (steel use stainless: SUS). However, the present invention is not limited thereto, and any material (for example, plastic) that is deformable along the shape of the tube main body 606 can be applied. For example, in a case where the thickness T (see FIG. 15) of the tube main body 606 is about 1 mm (for example, 1 mm at maximum), it is preferable that the thickness of the band-shaped member 642 is 300 μm or less. Examples of the high friction surface 644 include a resin layer obtained by coating an outer peripheral surface (first contact surface) of the spiral tube 640 with a resin such as urethane coating or silica coating, a rough surface formed on the first contact surface, and a resin layer obtained by coating the rough surface formed on the first contact surface with a resin. In a case where the above-described resin layer is formed, the formation can be performed by immersing the entire spiral tube 640 in the molten resin and drying the spiral tube 640. In this case, a resin layer serving as the high friction surface is also formed on a surface (inner peripheral surface) of the spiral tube 640 that is in contact with the inner tube 604.

In a case where the high friction surface is formed on the inner peripheral surface of the spiral tube 640 as described above, the spiral tube 640 and the inner tube 604 are closely attached to and frictionally engaged with each other via the high friction surface. In addition, in a case where the high friction surface is also formed on the outer peripheral surface of the inner tube 604, the spiral tube 640 and the inner tube 604 are closely attached to and frictionally engaged with each other via the respective high friction surfaces. In any case, the shape holding force of the tube main body 606 is further improved. As shown in FIGS. 16 and 17, in the spiral tube 640 configured as described above, two winding portion on each of the proximal end side and the distal end side are adhered to the proximal end side and the distal end side of the inner tube 604 by the adhesives 622 and 626. As a result, the spiral tube 640 is firmly adhered to the inner tube 604.

Next, the interlayer 614 shown in FIG. 14 will be described. The interlayer 614 is a sheet material 650 which is provided between the outer tube 602 and the inner tube 604 and is contactable with the shape deformable body 612 (the spiral tube 640). The sheet material 650 is arranged, for example, between the outer tube 602 and the spiral tube 640.

Figure 20:
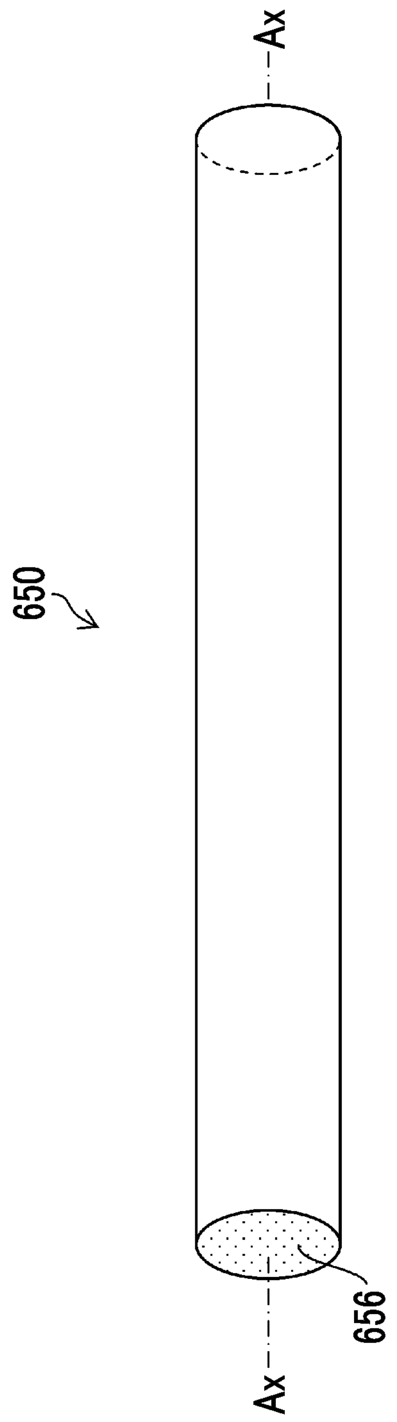
FIG. 20 is a perspective view of a sheet material.

FIG. 20 is a perspective view of the sheet material 650. As shown in FIG. 20, the sheet material 650 is formed into a cylindrical shape and is arranged along the direction of the axis Ax of the tube main body 606 (see FIG. 14). Accordingly, the outer peripheral surface (first contact surface) of the spiral tube 640 (FIG. 18) is covered with the sheet material 650. In addition, the sheet material 650 has flexibility to be deformable along the shape of the tube main body 606 (see FIG. 14). More specifically, the sheet material 650 has the flexibility and has a higher elastic modulus than the outer tube 602 (see FIG. 14) and the inner tube 604. The elastic modulus will be described later.

Figure 21:
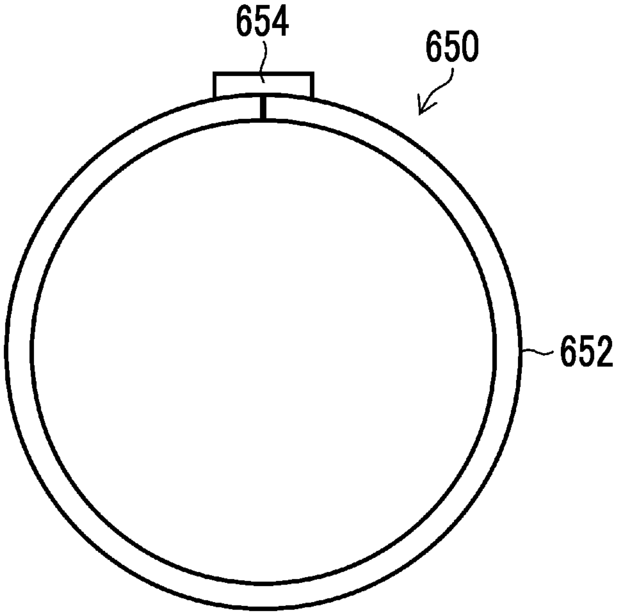
FIG. 21 is a front view of the sheet material shown in FIG. 20.
Figure 22:
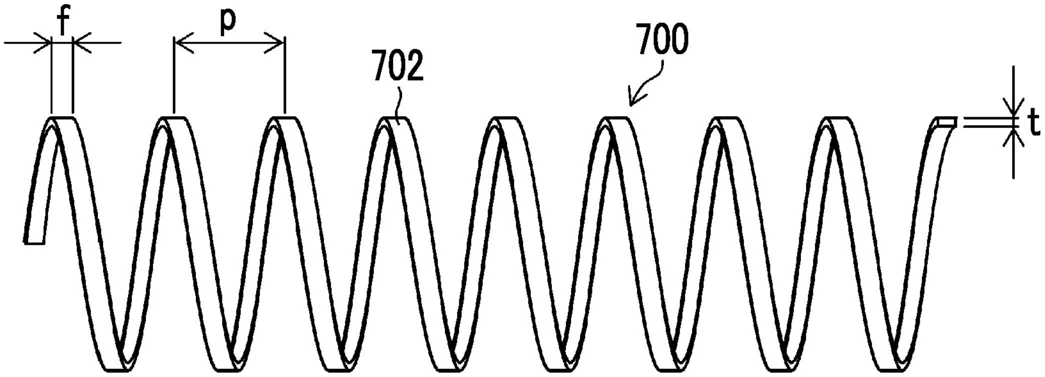
FIG. 22 is a side view showing a first modification example of the spiral tube.
Figure 23:
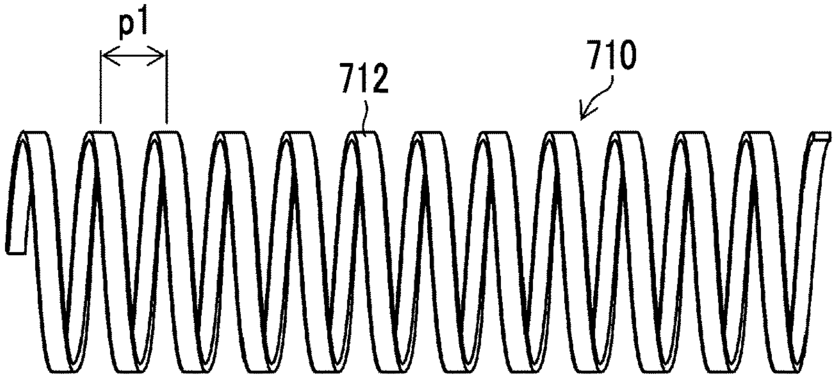
FIG. 23 is an external view showing a second modification example of the spiral tube.
Figure 24:
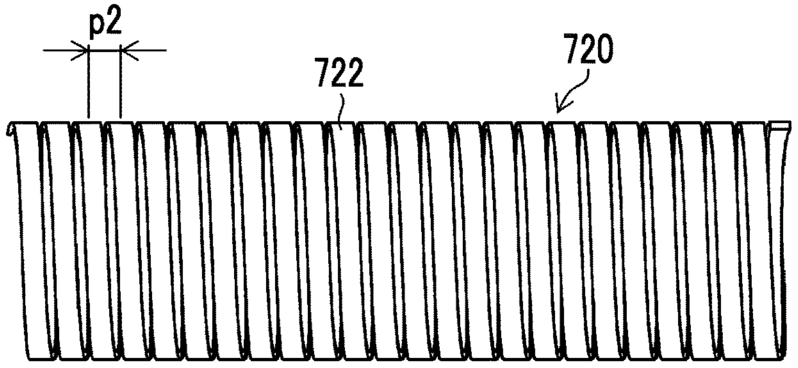
FIG. 24 is an external view showing a third modification example of the spiral tube.

For example, as in a front view of the sheet material 650 shown in FIG. 21, the sheet material 650 is formed by bending one sheet 652 having a rectangular shape into the cylindrical shape and adhering both adhering edge parts to each other with an adhesive 654. Note that the form of the sheet material 650 is not limited to the cylindrical shape, and may be, for example, a form in which the sheet 652 is bent into a C shape, or may be a form in which a plurality of striped sheets are inserted and arranged between the outer tube 602 and the spiral tube 130. Further, in the present example, the sheet material 650 will be described as an example of the interlayer 614, but the present invention is not limited thereto, and for example, a net-like or linear member can also be applied as long as the member is contactable with the shape deformable body 612 (the spiral tube 640). Hereinafter, the sheet material 650 applied as the interlayer 614 will be described.

The sheet material 650 is made of, for example, a resin such as urethane. However, the present invention is not limited to this, and for example, an aluminum vapor deposition film can also be applied. The aluminum vapor deposition film is a film in which aluminum (aluminum foil) is vapor-deposited (thermocompression-bonded) on a surface of a substrate film. By applying the aluminum vapor deposition film as the sheet material 650, the stiffness of the sheet material 650 can be increased. In this case, examples of the substrate film include a substrate film having heat sealability such as polyethylene terephthalate (PET) or polyethylene (PE). In addition, it is preferable that the sheet material 650 has a higher elastic modulus than the outer tube 602 and the inner tube 604, which is obtained by the methods described in JISK7161 (tensile test) or methods based thereon. Thus, the outer tube 602 and the inner tube 604 can be reinforced by the sheet material 650. That is, the tensile strength and the tensile stiffness of the tube main body 606 are increased by the sheet material 650. As a result, the forward mobility of the tube main body 606 in a case where the tube main body 606 is not hardened (in the flexible state) is improved. A material having an optimum elastic modulus can be selected by using the aluminum vapor deposition film or aluminum foil combined with various kinds of cloth and film.

For example, in a case where the thickness of the tube main body 606 is about 1 mm (for example, 1 mm at maximum), it is preferable that a thickness of the sheet material 650 is 300 μm or less. However, from the viewpoint of stiffness, it is preferable that the thickness of the sheet material 650 is thicker than the thicknesses of the outer tube 602 and the inner tube 604. In a case where the aluminum vapor deposition film is applied as the sheet material 650, the stiffness of the sheet material 650 can be changed by changing the substrate film. As a result, the hardness of the tube main body 606 during non-hardening can be tuned to the hardness suitable for a lower digestive tract such as the large intestine or an upper digestive tract such as an esophagus.

As shown in FIG. 20, the sheet material 650 has a high friction surface 656 on a surface (inner peripheral surface and second contact surface) that is in contact with the spiral tube 640 (see FIG. 17). Accordingly, in a case where the air in the inner space 608 (see FIG. 14) is discharged by the pump 38, the spiral tube 640 (see FIG. 17) and the sheet material 650 of the tube main body 606 (see FIG. 14) are closely attached to and frictionally engaged with each other via the respective high friction surfaces 644 and 656. As a result, since the shape (for example, a bent shape) of the spiral tube 640 is held not to be deformable, a shape holding force of the tube main body 606 in the high stiffness property state (during hardening) is further increased.

In the present example, although the form in which the high friction surfaces 644 and 656 are formed on both the first contact surface (outer peripheral surface) of the spiral tube 640 and the second contact surface (inner peripheral surface) of the sheet material 650 has been described as an example, the high friction surface may be formed on any one of the contact surfaces, and a form in which the high friction surface is formed only on the second contact surface (inner peripheral surface) of the sheet material 650 may be adopted. Further, the high friction surface is preferably formed on the entirety of any one of the contact surfaces, but the present invention is not limited thereto, and may be formed on a part of any one of the contact surfaces. That is, the high friction surface may be formed on at least a part of any one of the contact surfaces. However, by forming the high friction surfaces 644 and 656 on both the contact surfaces (preferably, the entirety of both the contact surfaces), the shape holding force of the tube main body 606 is improved. The method of forming the high friction surface 656 is the same as the method of forming the high friction surface 644. In addition, from the viewpoint of ensuring the flexibility of the tube main body 606 during non-hardening, a gap between the spiral tube 640 and the sheet material 650 is preferably about 50 μm to 500 μm.

Further, the high friction surface may be formed on at least a part of the outer peripheral surface of the sheet material 650 (preferably, the entire outer peripheral surface of the sheet material 650). As a result, the sheet material 650 and the outer tube 602 are closely attached to and frictionally engaged with each other via the high friction surface. Further, the high friction surface may be formed on at least a part of the inner peripheral surface of the outer tube 602 (preferably, the entire inner peripheral surface of the outer tube 602). As a result, the sheet material 650 and the outer tube 602 are closely attached to and frictionally engaged with each other via the respective high friction surfaces. In any case, the shape holding force of the tube main body 606 is further improved.

Next, an example of an operation in a case where the insertion part 14 of the endoscope 12 is guided to the large intestine 500 (see FIG. 6) by using the guide tube 600 will be described.

First, since the insertion part 14, the tube main body 606, the spiral tube 640, and the sheet material 650 each have the flexibility, in a case where the tube main body 606 and the insertion part 14 (see FIG. 1) inserted into the tube main body 606 are inserted along the large intestine 500 (see FIG. 6), the insertion part 14 is smoothly inserted along the bent shape of the large intestine 500.

Next, in a case where the pump 38 is operated in a state in which the tube main body 606 is disposed along the bent shape of the sigmoid colon 502 to suck the air in the inner space 608 from the pipe 40, the outer tube 602 is pressed against the sheet material 650, and the inner tube 604 is pressed against the spiral tube 640. As a result, the high friction surface 644 of the spiral tube 640 is closely attached to and frictionally engaged with the high friction surface 656 of the sheet material 650. As a result, the tube main body 606 is hardened in a shape corresponding to the bent shape of the sigmoid colon 502, and the shape is held, so that the insertability of the insertion part 14 into the sigmoid colon 502 is improved. In the above-described operation example, the tube main body 606 is hardened in a shape corresponding to the bent shape of the sigmoid colon 502, but the present invention is not limited to this operation example. For example, as another operation example, the tube main body 606 may be hardened in a state in which the sigmoid colon 502 is made substantially linear.

Next, the treatment of the lesion portion 506 of the transverse colon 504 is started by causing the bendable part 20 of the insertion part 14 to protrude forward from the distal end opening 10A of the guide tube 100 and leading out the treatment tool (not shown) forward from the treatment tool lead-out port (not shown) of the distal end hard part 18. In this case, since the insertability of the insertion part 14 into the sigmoid colon 502 is improved by the guide tube 600, the distal end hard part 18 can be positioned at an accurate treatment position, and as a result, it is possible to perform an accurate treatment on the lesion portion 506.

As described above, with the guide tube 600 according to the seventh embodiment, since the shape deformable body 612 that is deformable along the shape of the tube main body 606 is provided between the outer tube 602 and the inner tube 604, the insertability of the insertion part 14 of the endoscope 12 can be improved.

In addition, with the guide tube 600 according to the present example, since the configuration in which the spiral tube 640 and the sheet material 650 are arranged in the inner space 608 positioned between the outer tube 602 and the inner tube 604 is adopted, the following advantages are obtained. That is, the hardness of the tube main body 606 during hardening is higher than the hardness in a configuration including only the spiral tube 640 out of the spiral tube 640 and the sheet material 650 (that is, a configuration not including the sheet material 650). As a result, the insertability of the insertion part 14 is further improved. Further, in the configuration not including the sheet material 650, in a case in which the spiral tube 640 expands and contracts in the direction of the axis Ax by the operation of inserting the tube main body 606 into the large intestine 500, the forward mobility of the tube main body 606 may be affected in some cases. However, with the guide tube 600 according to the present example, expansion and contraction operation thereof can be suppressed by the frictional force between the spiral tube 640 and the sheet material 650. As a result, the forward mobility of the tube main body 606 during non-hardening is further improved.

In addition, it is preferable that the guide tube 600 according to the present example also comprises the mesh-like tube 56 shown in FIG. 2. Buckling of the tube main body 606 can be prevented by the mesh-like tube 56.

Further, in the above-described operation example, the treatment of the lesion portion 506 is performed in a state in which the tube main body 606 inserted into the large intestine 500 is in the hardened state only once, but the present invention is not limited to this operation example. For example, an operation of performing the treatment of the lesion portion 506 by moving the insertion part 14 and the tube main body 606 forward in a stepwise manner while changing the tube main body 606 inserted into the large intestine 500 between the non-hardened state and the hardened state a plurality of times may be performed. The operation in this case includes a step (insertion part insertion step) of inserting the insertion part 14 into the large intestine 500, a step (tube main body insertion step) of inserting the tube main body 606 into the large intestine 500 with respect to the insertion part 14 in a state in which the tube main body 606 into which the insertion part 14 has been inserted is in the non-hardened state, a step (insertion part forward movement step) of relatively moving the insertion part 14 forward with respect to the tube main body 606 in a state in which the tube main body 606 into which the insertion part 14 has been inserted is in the hardened state, and a step (tube main body forward movement step) of relatively moving the tube main body 606 forward with respect to the insertion part 14 in a state in which the tube main body 606 into which the insertion part 14 has been inserted is in the non-hardened state. The operation further includes a step (treatment step) of repeating the insertion part forward movement step and the tube main body forward movement step a plurality of times to bring the distal end hard part 18 close to the lesion portion 506 and treat the lesion portion 506. In such an operation, since the insertion part 14 has an effective length that is longer than the entire length of the tube main body 606 by 300 mm or more as described below, the operator can reliably grip the soft part 22 to perform the insertion operation without being obstructed by the tube main body 606.

Next, several modification examples of the spiral tube 640 which is the shape deformable body 612 will be described. FIGS. 22 to 26 are side views of spiral tubes 700, 710, 720, 730, and 740 that are examples of the modification example of the spiral tube 640.

Here, the stiffness and the flexibility of the spiral tube are controlled by the material, the thickness t, and a band width f of the band-shaped member constituting the spiral tube. As an example, in a case where the material is the stainless steel, the thickness t is about 200 μm to 300 μm, and the band width f is about 2 mm to 4 mm, the initial stiffness and flexibility required for the spiral tube can be secured. Further, the maximum curvature in a case where the spiral tube is bent is controlled by a winding pitch (spiral pitch) p of the band-shaped member. Therefore, in the spiral tube 700 according to the first modification example shown in FIG. 22, the spiral tube 710 according to the second modification example shown in FIG. 23, and the spiral tube 720 according to the third modification example shown in FIG. 24, the band-shaped members 702, 712, and 722 of the spiral tubes 700, 710, and 720 are respectively stainless steel and satisfy the suitable thickness t and the suitable band width f. Since the spiral tube 700 has the winding pitch p longer than winding pitches of the other spiral tubes 710 and 720 ($p>p1>p2$), the spiral tube 700 can be applied as, for example, a guide tube of a lower digestive tract endoscope that is required to have a large curvature. On the other hand, since the spiral tubes 710 and 720 have the winding pitches p1 and p2 smaller than the winding pitch of the spiral tube 700, for example, the spiral tubes can be applied as a guide tube of an upper digestive tract endoscope that can be used with a small curvature.

Figure 25:
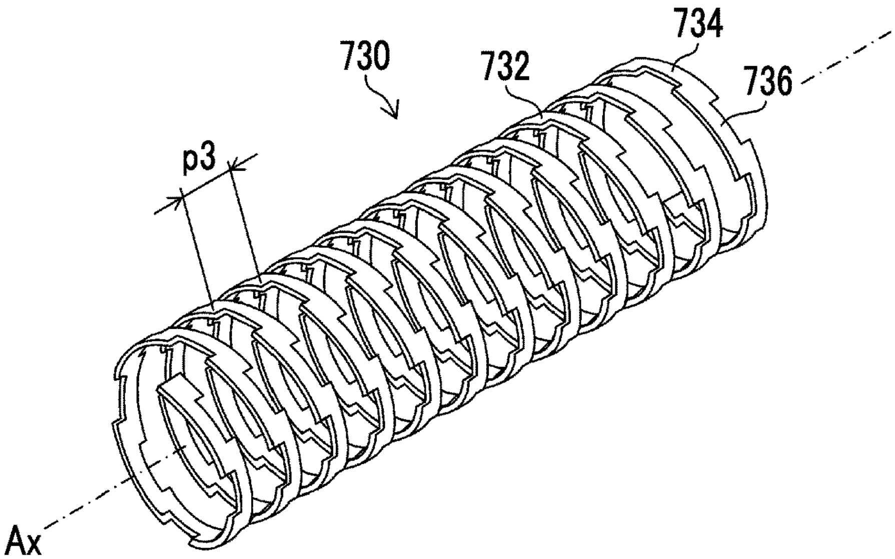
FIG. 25 is an external view showing a fourth modification example of the spiral tube.
Figure 26:
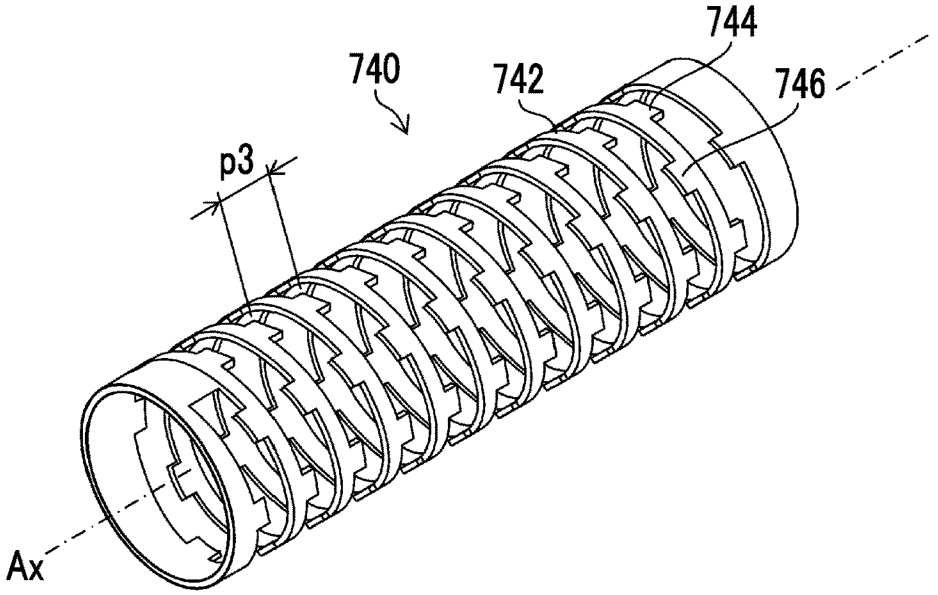
FIG. 26 is an external view showing a fifth modification example of the spiral tube.

On the other hand, band-shaped members 732 and 742 of the spiral tube 730 according to the fourth modification example shown in FIG. 25 and the spiral tube 740 according to the fifth modification example shown in FIG. 26 are stainless steel and satisfy the suitable thickness t and band width f, and further each have the same winding pitch p3. Therefore, in the spiral tubes 730 and 740, the band-shaped member 732 of the spiral tube 730 has bent parts 734 and 736 that are alternately bent toward the proximal end side and the distal end side of the axis Ax. In contrast, the band-shaped member 742 of the spiral tube 740 has protrusions 744 and 746 that alternately protrude toward the proximal end side and the distal end side of the axis Ax. With the spiral tube 730 including the bent parts 734 and 736 and the spiral tube 740 including the protrusions 744 and 746, the contact area with the sheet material can be increased compared to a spiral tube in which a striped band-shaped member is simply spirally wound. As a result, it is possible to further increase the shape holding force of the tube main body in the high stiffness property state (during hardening).

Figure 27:
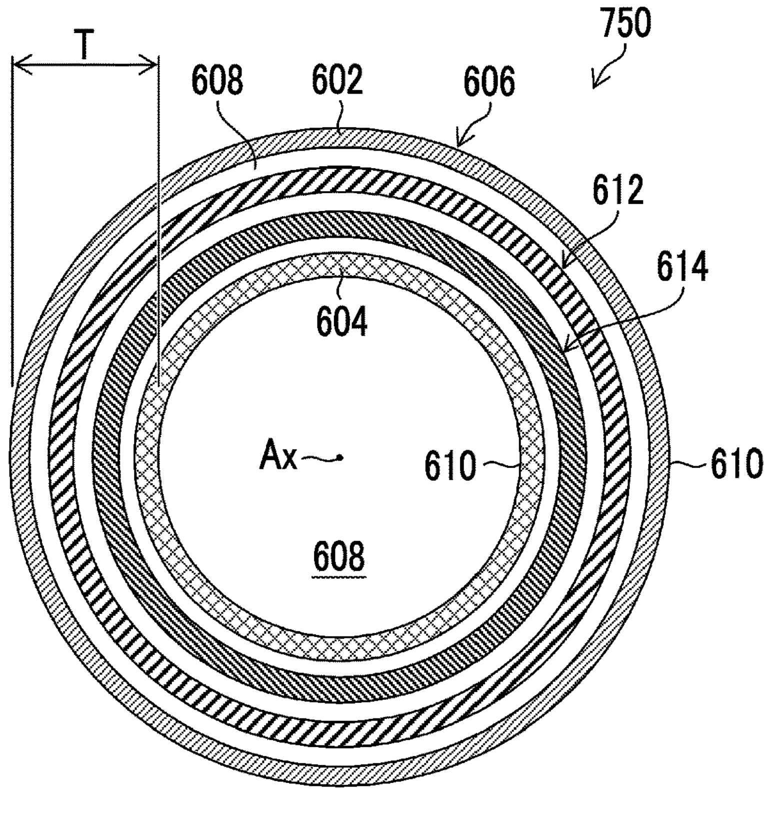
FIG. 27 is a vertical cross-sectional view showing a structure of a guide tube according to an eighth embodiment.

In the guide tube 600 according to the seventh embodiment, the configuration in which the interlayer 614 is arranged between the outer tube 602 and the shape deformable body 612 has been described as an example, but the present invention is not limited thereto. For example, as in a vertical cross-sectional view of a guide tube 750 according to an eighth embodiment shown in FIG. 27, a configuration in which the interlayer 614 is arranged between the inner tube 604 and the shape deformable body 612 may be adopted. However, from the viewpoint of the assemblability of the guide tube 600, for example, as shown in FIG. 14, a configuration in which the interlayer 614 is arranged in a wide space between the outer tube 602 and the shape deformable body 612 is preferable to a configuration in which the interlayer 614 is arranged in a narrow space between the inner tube 604 and the shape deformable body 612.

In addition, in the guide tube 600 according to the seventh embodiment, the configuration in which the shape deformable body 612 (spiral tube 640) and the interlayer 614 are provided has been described as an example, but the present invention is not limited thereto. For example, a guide tube having a configuration in which the shape deformable body 28 including the articulated ring member 42 (see FIG. 2) is incorporated into the configuration of the guide tube 600 can also be applied. In this case, the shape deformable body 28 may be arranged between the outer tube 602 and the interlayer 614, may be arranged between the inner tube 604 and the shape deformable body 612, or may be arranged between the shape deformable body 612 and the interlayer 614.

In the first to eighth embodiments described above, the example in which the tube main bodies 34 and 606 are switched between the flexible state and the high stiffness property state by supplying and discharging the air to and from the inner spaces 36 and 608 has been described, but in the medical instrument guide device according to the embodiment of the present invention, the hardness of the tube main body in the flexible state (initial stage) and the high stiffness property state (during hardening) can be adjusted by changing the materials of the articulated ring member and the spiral tube. For example, in a case where the articulated ring member and the spiral tube are made of a polypropylene resin, the above-described hardness can be adjusted by setting glass fibers contained in the polypropylene resin as short fibers having a short fiber length or as long fibers having a long fiber length. In this case, the former hardness is higher than the latter hardness. Since the hardness of the tube main body can be adjusted by changing the material as described above, the guide tube having the hardness corresponding to the applied technique can be prepared for each applied technique.

Hereinafter, an example of suitable dimensions of the insertion part 14 and the tube main bodies 34 and 606 (see FIG. 14) of the endoscope 12 shown in FIG. 1 will be described. First, the inner diameters of the tube main bodies 34 and 606 and an outer diameter of the insertion part 14 preferably have dimensions in which a clearance is formed between the tube main bodies 34 and 606 and the insertion part 14 in a state in which the insertion part 14 is inserted into the tube main bodies 34 and 606. That is, in a case where the inner diameters of the tube main bodies 34 and 606 are denoted by D1 and the outer diameter of the insertion part 14 is denoted by D2, it is preferable that D1 and D2 have a relationship of D1>D2. In addition, the clearance is more preferably 4 mm or less and even more preferably 1 mm or more and 4 mm or less.

The description will be made with specific dimensions as an example. In a case where the outer diameter of the insertion part 14 is, for example, 8 mm, the inner diameters of the tube main bodies 34 and 606 are more preferably 12 mm or less, and even more preferably 9 mm or more and 12 mm or less. Further, in a case where the outer diameter of the insertion part 14 is, for example, 13 mm, the inner diameters of the tube main bodies 34 and 606 are more preferably 17 mm or less, and even more preferably 14 mm or more and 17 mm or less.

By setting the clearance to 4 mm or less as described above, it is possible to prevent the body tissue (for example, an intestinal wall) from being interposed in the gaps between the tube main bodies 34 and 606 and the insertion part 14. In particular, in the step (tube main body forward movement step) of relatively moving the tube main bodies 34 and 606 forward with respect to the insertion part 14 in a state in which the tube main bodies 34 and 606 are in the non-hardened state, it is possible to prevent the body tissue (for example, the intestinal wall) from being interposed in the gaps. In addition, by setting the clearance to 1 mm or more, it is possible to smoothly perform the relative forward and backward movement operation of the insertion part 14 with respect to the tube main bodies 34 and 606.

Next, a relationship between a length of the insertion part 14 and lengths of the tube main bodies 34 and 606 will be described. It is preferable that the insertion part 14 has an effective length that is longer than the entire length of the tube main bodies 34 and 606 by 300 mm or more. Here, the effective length of the insertion part 14 refers to the length from the proximal end to the distal end of the insertion part 14.

The description will be made with specific dimensions as an example. In a case where the entire length of the tube main bodies 34 and 606 is, for example, 400 mm, it is preferable that the insertion part 14 has an effective length of 700 mm or more. Further, in a case where the entire length of the tube main bodies 34 and 606 is, for example, 700 mm, it is preferable that the insertion part 14 has an effective length of 1000 mm or more.

By making the effective length of the insertion part 14 longer than the entire length of the tube main bodies 34 and 606 by 300 mm or more in this manner, in a technique of inserting the tube main bodies 34 and 606 and the insertion part 14 into a body cavity, the operator can perform the insertion operation by reliably gripping the soft part 22 without being obstructed by the tube main bodies 34 and 606. The effective length of the insertion part 14 is, for example, 1200 mm. In addition, the tube main bodies 34 and 606 having the entire length of 400 mm can be used for the large intestine examination, and the tube main bodies 34 and 606 having the entire length of 700 mm can be used for the large intestine and small intestine examinations.

Figure 28:
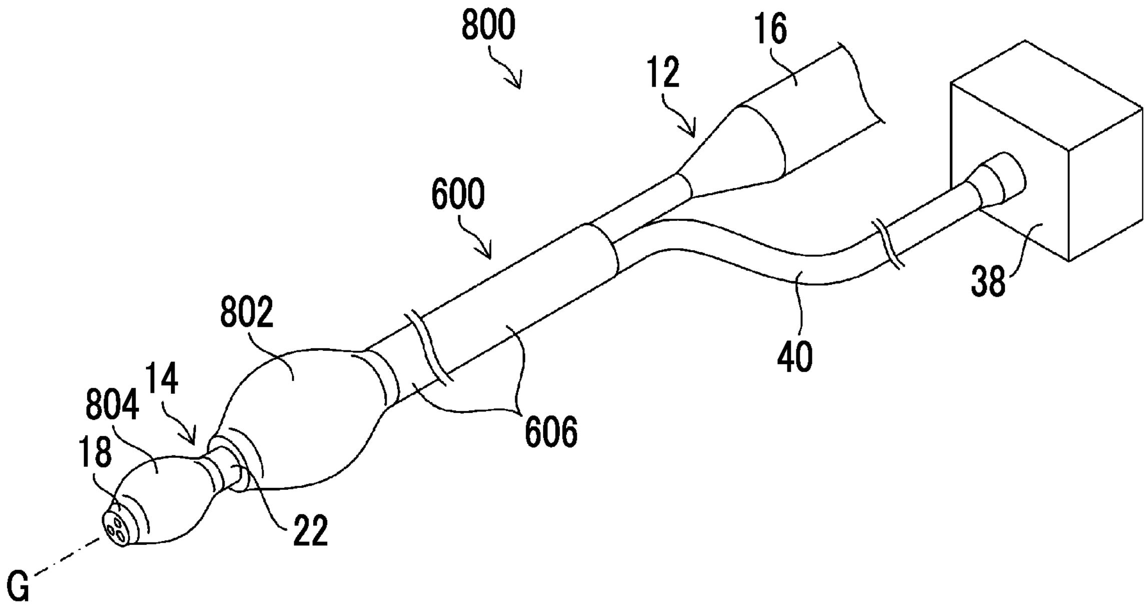
FIG. 28 is a perspective view of an endoscope apparatus according to the second embodiment of the present invention.

FIG. 28 is a perspective view of an endoscope apparatus 800 according to the second embodiment of the present invention.

As shown in FIG. 28, a guide tube applied to the endoscope apparatus 800 is a guide tube in which a balloon 802 is mounted on the guide tube 600 according to the seventh embodiment shown in FIG. 14. Further, an endoscope applied to the endoscope apparatus 800 is an endoscope in which a balloon 804 is mounted on the insertion part 14 of the endoscope 12 shown in FIG. 1. The balloon 802 is an example of an intracorporeal close attachment part according to the embodiment of the present invention, and is an example of a tube main body balloon according to the embodiment of the present invention. The balloon 804 is an example of an insertion part balloon according to the embodiment of the present invention. In the present example, the guide tube in which the balloon 802 is mounted on the guide tube 600 will be described as an example, but the present invention is not limited thereto, and a guide tube in which the balloon 802 is mounted on the guide tubes 10, 60, 70, 80, 90, and 100 according to the first to sixth embodiments or the guide tube 750 according to the eighth embodiment can also be applied.

Figure 29:
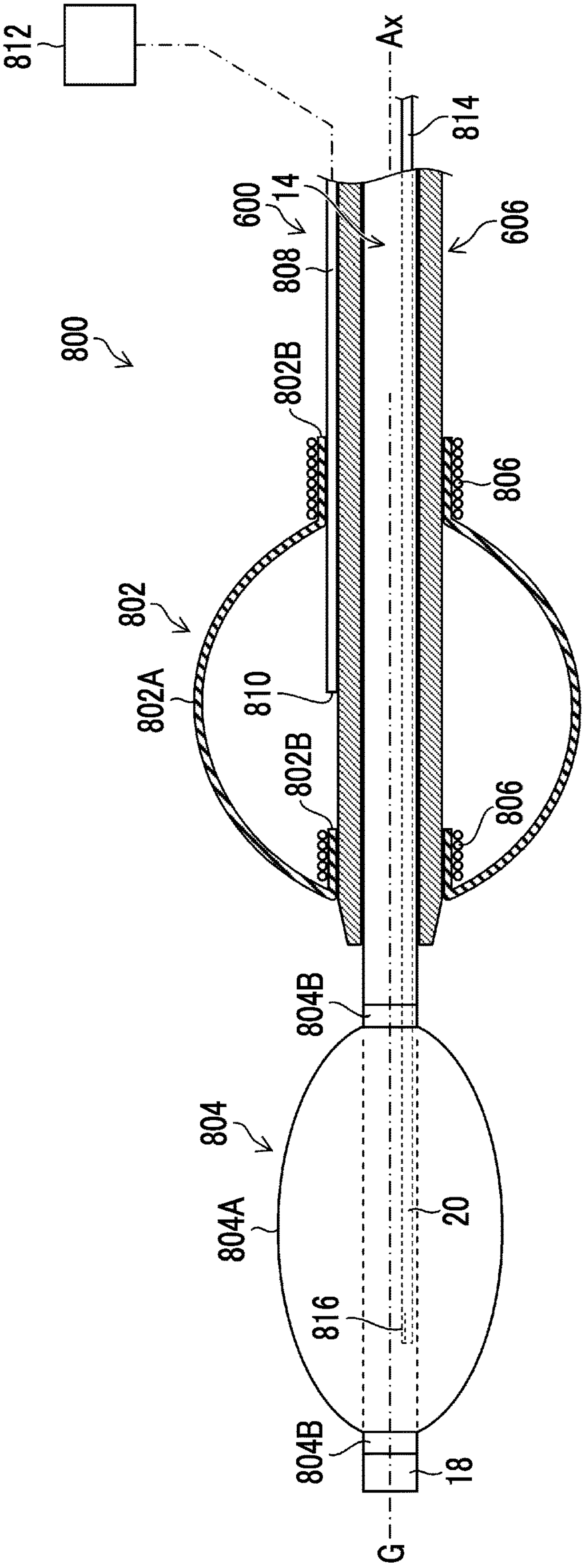
FIG. 29 is a cross-sectional view of the guide tube into which an insertion part is inserted.

FIG. 29 is a cross-sectional view of a main part of the guide tube 600 into which the insertion part 14 is inserted. Since the detailed structure of the guide tube 600 has already been described in FIG. 14, the illustration of the detailed structure of the guide tube 600 in FIG. 29 will be omitted, and the description thereof will be also omitted.

As shown in FIGS. 28 and 29, the balloon 802 that is expandable and contractible is attachably and detachably mounted on the distal end part of the tube main body 606 of the guide tube 600. The balloon 802 is made of an elastic body such as rubber, and includes a bulging part 802A at the center and attachment parts 802B and 802B at both ends thereof. The attachment parts 802B and 802B are both fixed to an outer surface of the tube main body 606 by winding a thread 806.

As shown in FIG. 29, an air tube 808 is attached to the outer surface of the tube main body 606 along the axis Ax, and a distal end of the air tube 808 is open in the bulging part 802A and is formed as an air supply and suction port 810. Further, a proximal end of the air tube 808 is connected to a pump 812 arranged outside the tube main body 606. The pump 812 is a multi-type air pump that can supply (pressurize) and suck air. In a case where air is supplied from the pump 812 to the air tube 808, air is blown out from the air supply and suction port 810, and the bulging part 802A expands. On the other hand, in a case where the air is sucked from the pump 812, the air is sucked from the air supply and suction port 810 via the air tube 808, and the bulging part 802A contracts.

Figure 30:
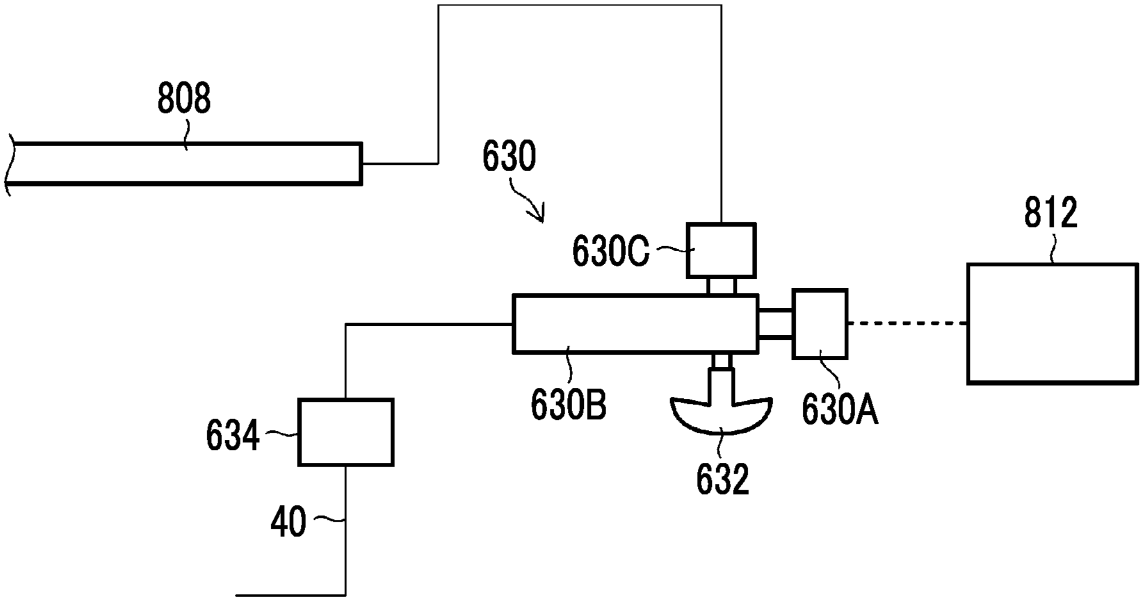
FIG. 30 is a piping diagram in a case where a pump is used in combination.

Here, although the pump 38 shown in FIG. 14 is connected to the tube main body 606 via the pipe 40, the pump 812 shown in FIG. 29 can be used instead of the pump 38. In this case, for example, as in a piping diagram shown in FIG. 30, the pump 812 is connected to a first port 630A of the three way stopcock 630, the pipe 40 is connected to a second port 630B, and the air tube 808 is connected to a third port 630C. Further, the pipe 40 is provided with a valve 634 for opening the inner space 608 (see FIG. 14) to the atmosphere and allowing the atmosphere to flow into the inner space 608.

In a case where the cock 632 of the three way stopcock 630 is manually operated to cause the first port 630A and the second port 630B to communicate with each other, the air in the inner space 608 (see FIG. 14) can be sucked by the pump 812 switched to the suction side. Accordingly, the tube main body 606 is changed from the softened state to the hardened state. In addition, by opening the valve 634, the inner space 608 can be opened to the atmosphere and the atmosphere is allowed to flow into the inner space 608. Accordingly, the tube main body 606 is changed from the hardened state to the non-hardened state.

In a case where the cock 632 of the three way stopcock 630 is manually operated to cause the first port 630A and the third port 630C to communicate with each other, the air can be blown out from the air supply and suction port 810 (see FIG. 29) by the pump 812 switched to the pressurization side. Accordingly, the bulging part 802A expands. In a case where the first port 630A and the third port 630C communicate with each other as described above, the air can be sucked from the air supply and suction port 810 (see FIG. 29) by the pump 812 switched to the suction side. Accordingly, the bulging part 802A contracts.

Instead of the manual switching operation using the three way stopcock 630, the switching operation can also be automated. In this case, for example, the pipe 40 and the air tube 808 need only be connected to the pump 812 via separate electromagnetic valves, the valve 634 need only be formed of an electromagnetic valve, and an opening and closing timing of the electromagnetic valves and a switching timing of the pressurization and suction of the pump 812 need only be controlled by a controller. Thus, the switching operation described above can be automated.

Returning to FIGS. 28 and 29, a balloon 804 that is expandable and contractible is attachably and detachably mounted on the distal end part of the insertion part 14. The balloon 804 is made of an elastic body such as rubber, and includes a bulging part 804A at the center and attachment parts 804B and 804B at both ends thereof. The attachment parts 804B and 804B are both fixed to an outer surface of the bendable part 20.

As shown in FIG. 29, an air tube 814 is inserted into the insertion part 14 along a longitudinal axis G of the insertion part 14, and a distal end of the air tube 814 is open in the outer surface of the bendable part 20 positioned in the bulging part 804A and is formed as an air supply and suction port 816. Additionally, a proximal end of the air tube 814 is connected to a pump (not shown) arranged outside the insertion part 14. Accordingly, in a case where the air is supplied from the pump to the air tube 814, the air is blown out from the air supply and suction port 816, and the bulging part 804A expands. On the other hand, in a case where the air is sucked from the pump, the air is sucked from the air supply and suction port 816 via the air tube 814, and the bulging part 804A contracts. It is preferable to use the pump 812 for the balloon 802 as the pump for the balloon 804. In this case, by adopting the configuration in which the air tube 814 is connected to the pump 812 via the electromagnetic valve or the like, the supply and suction of the air to and from the balloon 804 can be performed. In a case where the pump 812 for the balloon 802 is used as the pump for the balloon 804 as described above, it is possible to reduce the initial cost and the running cost of the endoscope apparatus 800.

Figure 31:
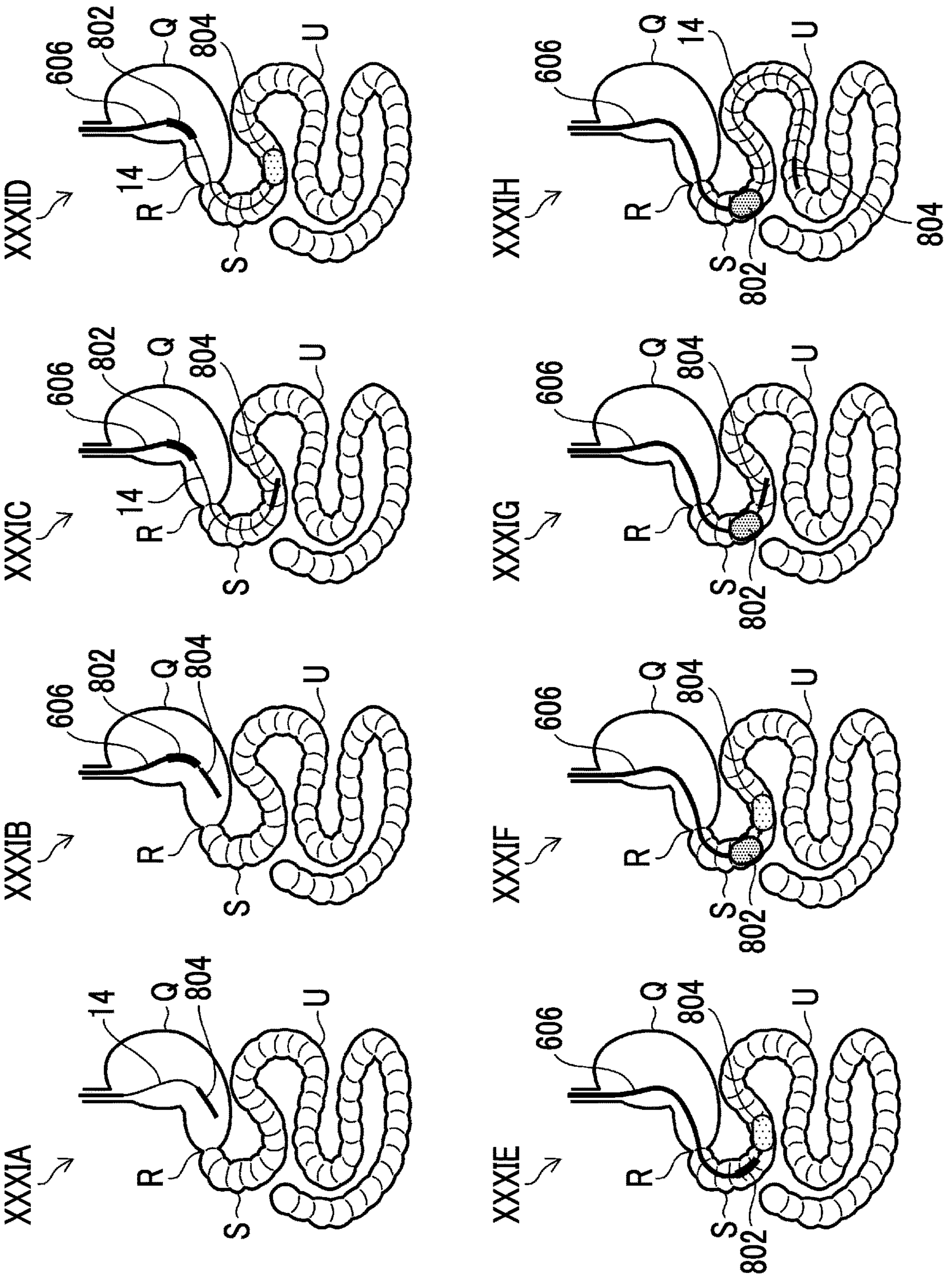
FIG. 31 is an explanatory view showing a technique procedure of the endoscope apparatus shown in FIG. 28.
Figure 32:
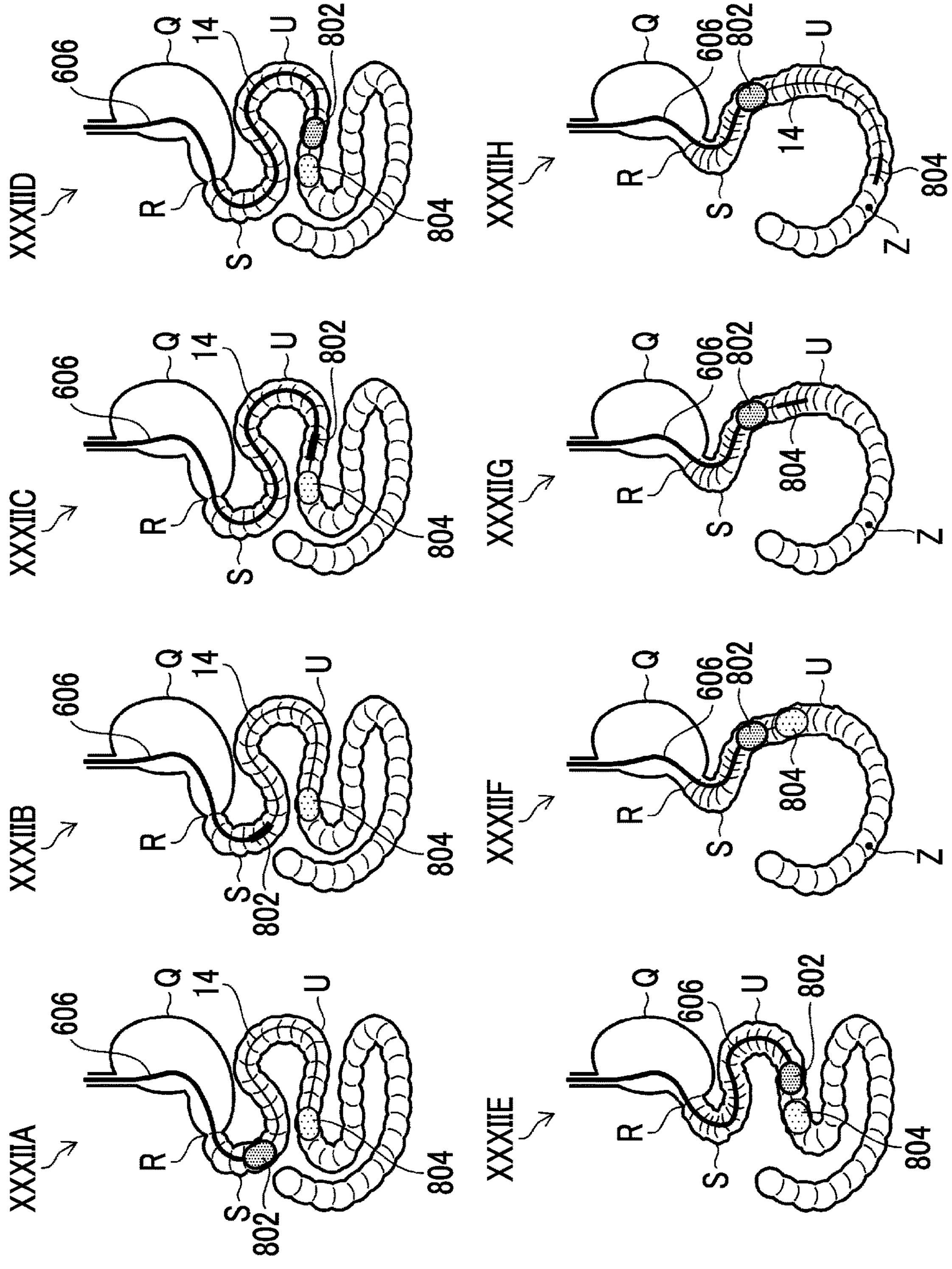
FIG. 32 is an explanatory view showing a technique procedure of the endoscope apparatus shown in FIG. 28.

Next, an operation method of the endoscope apparatus 800 shown in FIG. 28 will be described with reference to FIGS. 31 and 32. From XXXIA of FIG. 31 to XXXIIH of FIG. 32, an example of a technique procedure in a case where the endoscope apparatus 800 is applied as a small intestine endoscope apparatus is shown in time series. In FIGS. 31 and 32, reference numeral Q denotes a stomach, reference numeral R denotes a pylorus, reference numeral S denotes a duodenum, reference numeral U denotes a small intestine, and reference numeral Z denotes a lesion portion.

First, in a state in which the insertion part 14 is inserted into the tube main body 606 and in a state in which the balloon 804 is contracted, the insertion part 14 is inserted into the body. That is, the distal end part of the insertion part 14 is inserted into the stomach Q from a mouth of a subject via an esophagus. XXXIA of FIG. 31 shows a state in which the distal end part of the insertion part 14 is inserted into the stomach Q.

Next, in a state in which the balloon 802 is in the contraction state and the tube main body 606 is in the non-hardened state, the tube main body 606 is inserted into the body along the insertion part 14. That is, the distal end part of the tube main body 606 is inserted into the stomach Q from the mouth of the subject via the esophagus. XXXIB of FIG. 31 shows a state in which the distal end part of each of the insertion part 14 and the tube main body 606 is inserted into the stomach Q.

Next, as shown in XXXIC of FIG. 31, the insertion part 14 is relatively moved forward with respect to the tube main body 606 to insert the distal end part of the insertion part 14 into the duodenum S via the pylorus R. A state in which the insertion part 14 is inserted along the bent shape of the duodenum S and the distal end part of the insertion part 14 is inserted into the ascending portion of the duodenum S is shown in XXXIC of FIG. 31.

Next, as shown in XXXID of FIG. 31, the balloon 804 is expanded to fix the insertion part 14 inside the body (insertion part fixing step). XXXID of FIG. 31 shows a state in which the balloon 804 is closely attached to the ascending portion of the duodenum S and the insertion part 14 is fixed to the duodenum S.

Next, as shown in XXXIE of FIG. 31, the tube main body 606 is relatively moved forward with respect to the insertion part 14 in a state in which the balloon 802 is in the contraction state and the tube main body 606 is in the non-hardened state (tube main body forward movement step). XXXIE of FIG. 31 shows a state in which the tube main body 606 is inserted along the bent shape of the duodenum S and the distal end part of the tube main body 606 is inserted to the front of the balloon 804 of the insertion part 14.

Next, the tube main body 606 is changed from the non-hardened state to the hardened state. That is, the air in the inner space 608 (see FIG. 14) of the tube main body 606 is sucked by the pump 812 (see FIG. 30), and thus the tube main body 606 is hardened. XXXIE of FIG. 31 shows a state in which the tube main body 606 is hardened in a shape along the bent shape of the duodenum S.

Next, as shown in XXXIF of FIG. 31, the balloon 802 expanded to fix the tube main body 606 inside the body in a state in which the tube main body 606 is in the hardened state (tube main body fixing step). XXXIF of FIG. 31 shows a state in which the balloon 802 is closely attached to the ascending portion of the duodenum S and the tube main body 606 is fixed to the duodenum S.

Next, as shown in XXXIG of FIG. 31, the balloon 804 is contracted. XXXIG of FIG. 31 shows a state in which the balloon 804 contracts and the fixation of the insertion part 14 to the duodenum S is released.

Next, as shown in XXXIH of FIG. 31, the insertion part 14 is relatively moved forward with respect to the tube main body 606 in a state in which the balloon 804 is in the contraction state (insertion part forward movement step). XXXIH of FIG. 31 shows a state in which the distal end part of the insertion part 14 is inserted into a deep portion of the small intestine U along the bent shape of the small intestine U. In a case where the insertion part 14 moves forward, since the tube main body 606 is hardened in a shape along the bent shape of the duodenum S, the distal end part of the insertion part 14 can be stably moved forward toward the deep portion of the small intestine U.

Next, as shown in XXXIIA of FIG. 32, the balloon 804 is expanded to fix the insertion part 14 inside the body (insertion part fixing step). XXXIIA of FIG. 32 shows a state in which the balloon 804 is closely attached to the small intestine U and the insertion part 14 is fixed to the small intestine U.

Next, the balloon 802 is contracted as shown in XXXIIB of FIG. 32. XXXIIB of FIG. 32 shows a state in which the balloon 802 contracts and the fixation of the tube main body 606 to the duodenum S is released.

Next, the tube main body 606 is changed from the hardened state to the non-hardened state. That is, the tube main body 606 is softened by opening the inner space 608 (see FIG. 14) of the tube main body 606 to the atmosphere and allowing the atmosphere to flow into the inner space 608.

Next, as shown in XXXIIC of FIG. 32, the tube main body 606 is relatively moved forward with respect to the insertion part 14 in a state in which the balloon 802 is in the contraction state and the tube main body 606 is in the non-hardened state (tube main body forward movement step). XXXIIC of FIG. 32 shows a state in which the tube main body 606 is inserted along the bent shape of the small intestine U and the distal end part of the tube main body 606 is inserted to the front of the balloon 804 of the insertion part 14.

Next, as shown in XXXIID of FIG. 32, the balloon 802 expanded to fix the tube main body 606 inside the body. XXXIID of FIG. 32 shows a state in which the balloon 802 is closely attached to the small intestine U and the tube main body 606 is fixed to the small intestine U.

Next, as shown in XXXIIF from the XXXIIE of FIG. 32, the tube main body 606 and the insertion part 14 are integrally pulled in an outside direction of the body. XXXIIF of FIG. 32 shows a state in which the small intestine U is pulled toward the stomach Q side in a state in which the balloons 802 and 804 are closely attached to the small intestine U. Since the small intestine U contracts in a length direction by this technique, the lesion portion Z of the small intestine U can be made to approach the distal end part of the insertion part 14.

Next, the tube main body 606 is changed from the non-hardened state to the hardened state. That is, the air in the inner space 608 (see FIG. 14) of the tube main body 606 is sucked by the pump 812 (see FIG. 30), and thus the tube main body 606 is hardened. XXXIIF of FIG. 32 shows a state in which the tube main body 606 is hardened in a shape along the bent shape of the contracted small intestine U.

Next, the balloon 804 is contracted as shown in XXXIIG of FIG. 32. A state in which the balloon 804 contracts and the fixation of the insertion part 14 to the small intestine U is released is shown in the XXXIIG of FIG. 32.

Next, as shown in XXXIIH of FIG. 32, the insertion part 14 is relatively moved forward with respect to the tube main body 606 in a state in which the balloon 804 is in the contraction state (insertion part forward movement step). XXXIIH of FIG. 32 shows a state in which the distal end part of the insertion part 14 is inserted along the bent shape of the small intestine U and inserted to the vicinity of the lesion portion Z. In a case where the insertion part 14 moves forward, since the tube main body 606 is hardened in a shape along the bent shape of the small intestine U, the distal end part of the insertion part 14 can be stably moved forward toward the deep portion of the lesion portion Z.

Next, in a case where the distal end part of the insertion part 14 reaches the lesion portion Z, the balloon 804 is expanded and is closely attached to the small intestine U, thereby fixing the distal end part of the insertion part 14 to the small intestine U. Thereafter, the treatment tool (not shown) is inserted from the proximal end side of the insertion part 14, the treatment tool is led out from the treatment tool lead-out port (not shown) on the distal end side of the insertion part 14, and treatment of the lesion portion Z is started. Since the tube main body 606 is fixed to the small intestine U by the balloon 802 and the distal end part of the insertion part 14 is fixed to the small intestine U by the balloon 804 during the treatment of the lesion portion Z with the treatment tool, the distal end part (distal end hard part 18) of the insertion part 14 can be positioned at an accurate treatment position. As a result, it is possible to perform an accurate treatment on the lesion portion 506.

In a case where the treatment of the lesion portion Z with the treatment tool is finished, the balloon 804 of the insertion part 14 is contracted to release the fixation of the insertion part 14 to the small intestine U. The tube main body 606 is changed from the hardened state to the non-hardened state, and the balloon 802 is contracted to release the fixation of the tube main body 606 to the small intestine U. Thereafter, the insertion part 14 and the tube main body 606 are integrally removed to the outside of the body. The above is an example of the operation method of the endoscope apparatus 800.

As described above, with the endoscope apparatus 800 adopting the configuration in which the balloon 804 is provided in the insertion part 14 and the balloon 802 is provided in the tube main body 606, the distal end part of the insertion part 14 can be stably moved forward toward the lesion portion Z existing in the deep portion of the small intestine U by selectively executing a step of expanding and contracting the balloon 804 (first expansion and contraction step), a step of expanding and contracting the balloon 802

(second expansion and contraction step), a step of changing the tube main body 606 between the non-hardened state and the hardened state (hardness changing step), and a step of relatively moving the insertion part 14 and the tube main body 606 forward and backward (forward and backward movement step). In addition, it is possible to accurately perform the treatment of the lesion portion Z with the treatment tool.

Although the balloon 804 is provided on the endoscope 12 side in the above-described embodiment, the present invention is not limited thereto. For example, the balloon 804 may be provided only on the guide tube 600 side without providing the balloon 802 on the endoscope 12 side. An operation method of the endoscope apparatus in this form (that is, the form in which the balloon 804 is provided only on the guide tube 600 side) is basically the same as the operation methods shown in FIGS. 31 and 32, but the insertion part 14 can be fixed to the intestinal tract by performing an operation of bending the bendable part 20 and hooking the distal end part (distal end hard part 18) to the intestinal tract or the like instead of expanding the balloon 802 provided on the endoscope 12 side.

Hereinafter, several modification examples of the tube main body balloon mounted on the tube main body 606 will be described.

Figure 33:
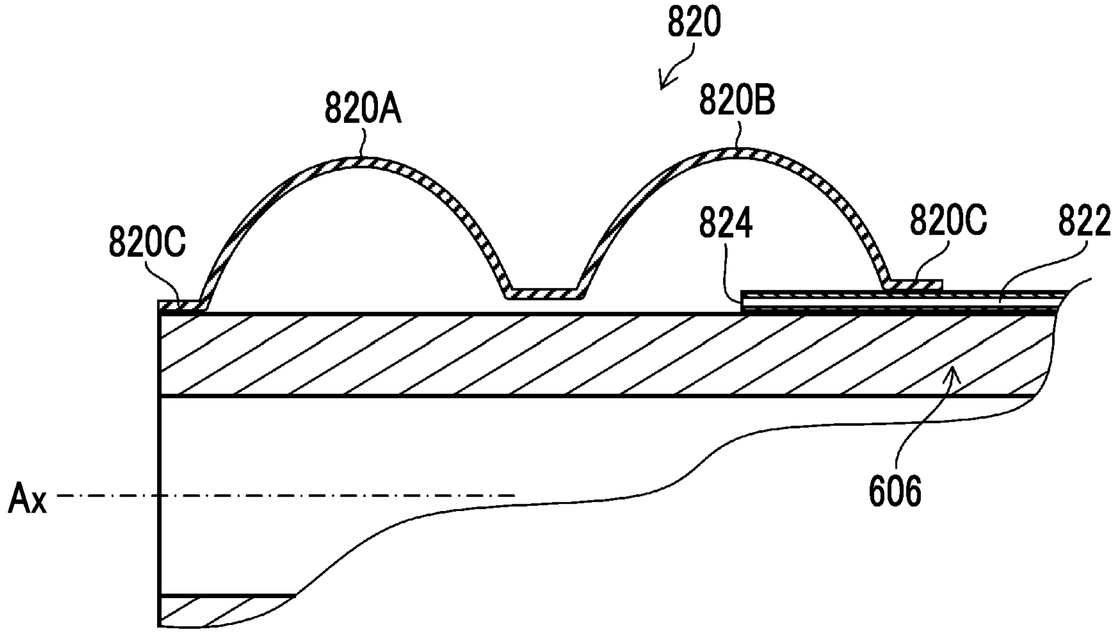
FIG. 33 is a cross-sectional view showing a balloon according to a first modification example.

FIG. 33 is a cross-sectional view showing a main part of a balloon 820 according to a first modification example. The balloon 820 is made of an elastic material such as rubber, and includes two bulging parts 820A and 820B and attachment parts 820C and 820C. By fixing the attachment parts 820C, 820C to the outer surface of the tube main body 606, the bulging part 820B is attached to the distal end side of the tube main body 606, and the bulging part 820B is attached to the proximal end side of the tube main body 606.

As shown in FIG. 33, an air tube 822 is attached to the outer surface of the tube main body 606 along the axis Ax, and a distal end of the air tube 822 is open in the bulging part 820A and is formed as an air supply and suction port 824. Further, a proximal end of the air tube 822 is connected to the pump (not shown) arranged outside the tube main body 606. In a case where air is supplied from this pump to the air tube 822, the air is blown out from the air supply and suction port 824, and the bulging parts 820A and 820B expand. On the other hand, in a case where the air is sucked from the pump, the air is sucked from the air supply and suction port 824 via the air tube 822, and the bulging parts 820A and 820B contract. Even the balloon 820 including the two bulging parts 820A and 820B can be applied as the tube main body balloon.

Figure 34:
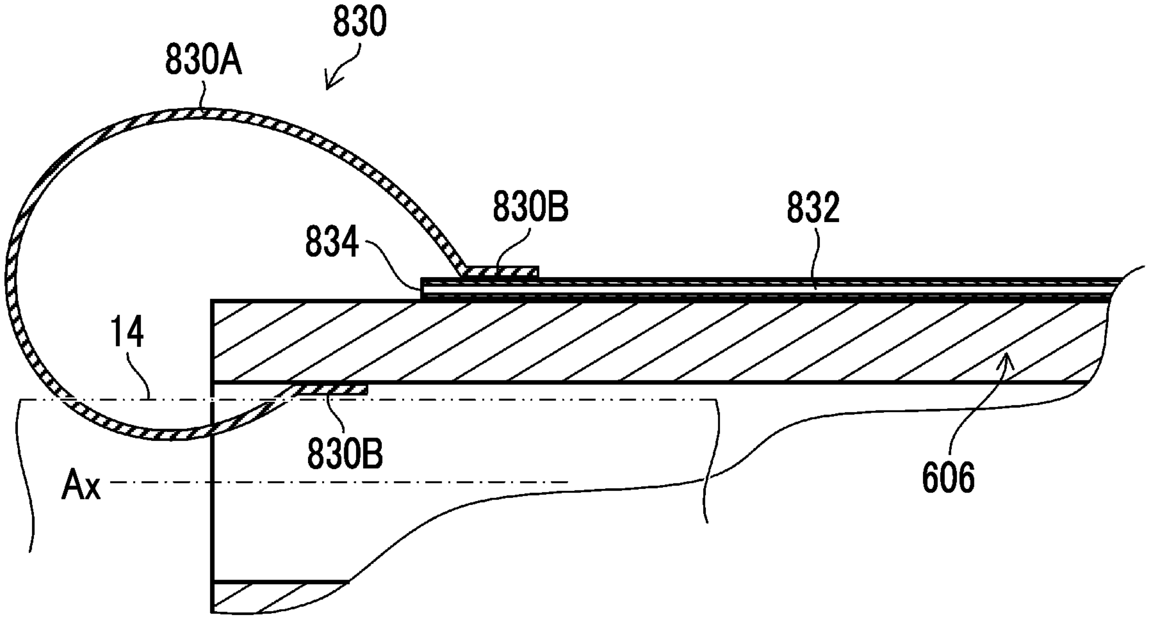
FIG. 34 is a cross-sectional view showing a balloon according to a second modification example.

FIG. 34 is a cross-sectional view showing a main part of a balloon 830 according to a second modification example. The balloon 830 includes a bulging part 830A at the center and attachment parts 830B and 830B at both ends thereof, the attachment part 830B on the distal end side is fixed to an inner surface of the tube main body 606, and the attachment part 830B on the proximal end side is fixed to the outer surface of the tube main body 606. With the balloon 830, in a case where the bulging part 830A expands, the bulging part 830A can expand both radially outward and radially inward of the tube main body 606. As a result, the expanded bulging part 830A can be closely attached to both the intestinal wall (not shown) and the insertion part 14.

As shown in FIG. 34, an air tube 832 is attached to the outer surface of the tube main body 606 along the axis Ax, and a distal end of the air tube 832 is open in the bulging part 830A and is formed as an air supply and suction port 834. Further, a proximal end of the air tube 832 is connected to the pump (not shown) arranged outside the tube main body 606. In a case where air is supplied from this pump to the air tube 832, air is blown out from the air supply and suction port 834, and the bulging part 830A expands. In this case, since a part of the bulging part 830A is closely attached to the insertion part 14, it is possible to prevent the body tissue (for example, the intestinal wall) from being interposed in the gap between the tube main body 606 and the insertion part 14. On the other hand, in a case where the air is sucked from the pump, the air is sucked from the air supply and suction port 834 via the air tube 832, and the bulging part 830A contracts. Even the balloon 830 including such a bulging part 830A can be applied as the tube main body balloon.

Figure 35:
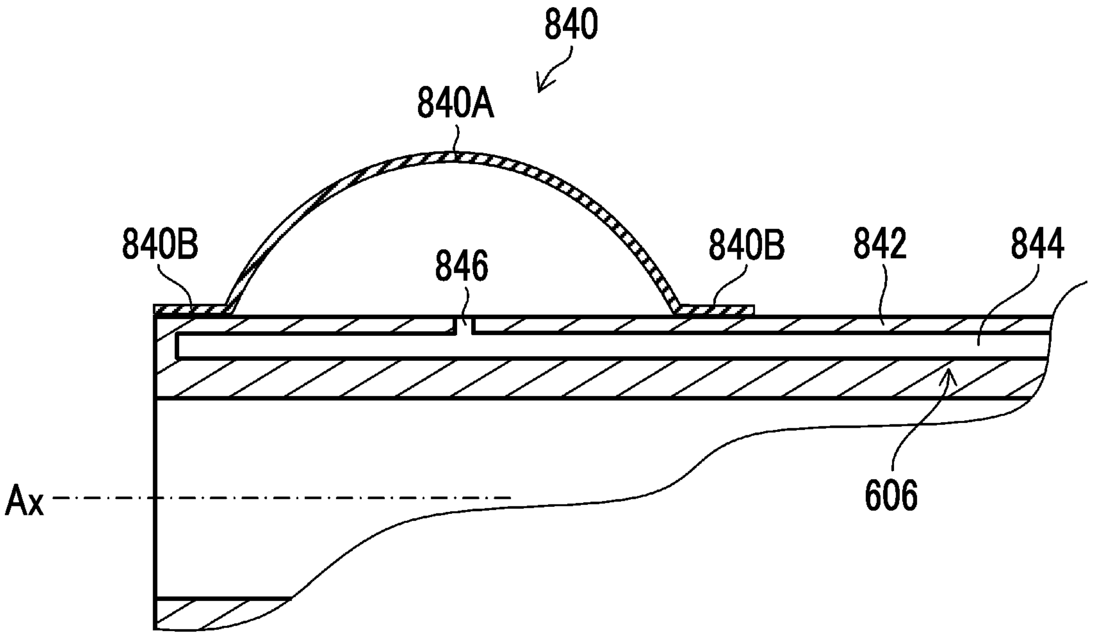
FIG. 35 is a cross-sectional view showing a balloon according to a third modification example.

FIG. 35 is a cross-sectional view showing a main part of a balloon 840 according to a third modification example. Before describing the balloon 840, the tube main body 606 according to the present example has a tubular body 842 that accommodates the tube main body 606 inside. A space 844 between the tube main body 606 and the tubular body 842 is formed as the sealed space, and the space 844 is configured as a ventilation path and is connected to a pump (not shown). The balloon 840 is attached to a distal end part of the tubular body 842, and an air supply and suction port 846 is formed at the distal end part of the tubular body 842 positioned in a bulging part 840A of the balloon 840. Accordingly, the space 844 and the bulging part 840A communicate with each other via the air supply and suction port 846. The balloon 840 is mounted on the tube main body 606 by fixing attachment parts 840B and 840B at both ends of the bulging part 840A to the outer surface of the tubular body 842.

With the balloon 840 shown in FIG. 35, in a case where air is supplied from the pump to the space 844, the air is blown out from the air supply and suction port 846, and the bulging part 840A expands. On the other hand, in a case where the air is sucked from the pump, the air is sucked from the air supply and suction port 846 via the space 844, and the bulging part 840A contracts. Even the balloon 840 mounted on the distal end part of the tubular body 842 as described above can be applied as the tube main body balloon.

Figure 36:
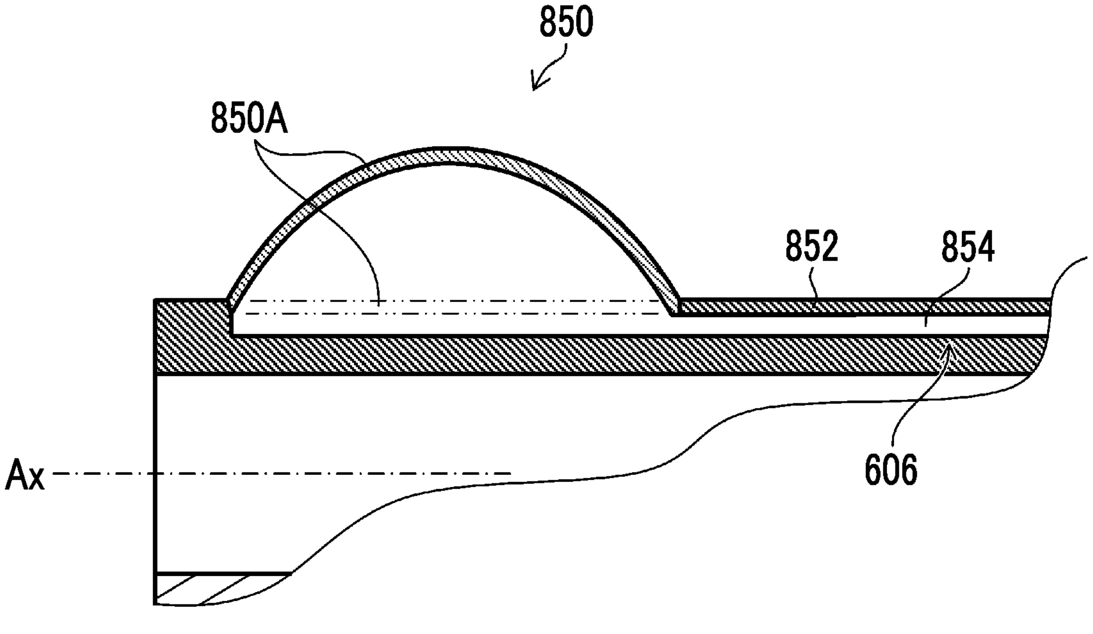
FIG. 36 is a cross-sectional view showing a balloon according to a fourth modification example.

FIG. 36 is a cross-sectional view showing a main part of a balloon 850 according to a fourth modification example. Before describing the balloon 850, the tube main body 606 according to the present example has a tubular body 852 that accommodates the tube main body 606 inside. A space 854 between the tube main body 606 and the tubular body 852 is formed as the sealed space, and the space 854 is configured as a ventilation path and is connected to a pump (not shown). Further, a distal end part of the tubular body 852 is formed of an elastic body such as rubber, and the distal end part is formed as a bulging part 850A of the balloon 850. Further, a portion of the tubular body 852 other than the distal end part functioning as the bulging part 850A is made of a raw material that is not expandable and contractible (for example, hard plastic).

With the balloon 850 shown in FIG. 36, in a case where air is supplied from the pump to the space 854, the distal end part (that is, the bulging part 850A) of the tubular body 852 shown by a two dot dashed line in FIG. 36 expands as shown by a solid line in FIG. 36. On the other hand, in a case where the air is sucked from the pump, the air is sucked via the space 854, and the bulging part 850A contracts as shown by a two dot dashed line in FIG. 36. Even the balloon 850 in which the bulging part 850A is formed in the tubular body 852 as described above can be applied as the tube main body balloon.

Figure 37:
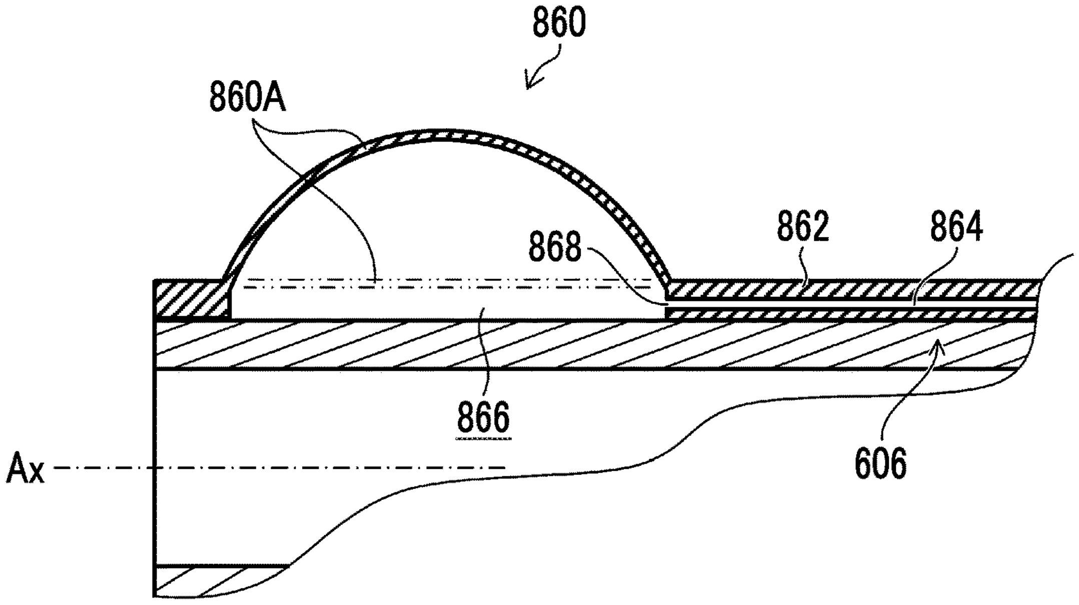
FIG. 37 is a cross-sectional view showing a balloon according to a fifth modification example.

FIG. 37 is a cross-sectional view showing a main part of a balloon 860 according to a fifth modification example. Before describing the balloon 860, the tube main body 606 according to the present example has a tubular body 862 that accommodates the tube main body 606 inside. A thin-wall part that functions as a bulging part 860A of the balloon 860 is formed at the distal end part of the tubular body 862. A sealed space 866 is formed between the bulging part 860A and the tube main body 606.

As shown in FIG. 37, a multi-lumen tube 864 is formed in the tubular body 862 along the axis Ax. A distal end of the multi-lumen tube 864 is open to the sealed space 866 and formed as an air supply and suction port 868. In addition, a proximal end of the multi-lumen tube 864 is connected to a pump (not shown).

With the balloon 860 shown in FIG. 37, in a case where air is supplied from the pump to the multi-lumen tube 864, the air is ejected from the air supply and suction port 868 to the sealed space 866, and the bulging part 860A expands as shown by a solid line in FIG. 37. On the other hand, in a case where the air is sucked from the pump, the air is sucked from the air supply and suction port 868 via the multi-lumen tube 864, and the bulging part 860A contracts as shown by a two dot dashed line in FIG. 37. Even the balloon 860 in which the bulging part 860A that is thin wall is formed in the tubular body 862 as described above can be applied as the tube main body balloon.

Figure 38:
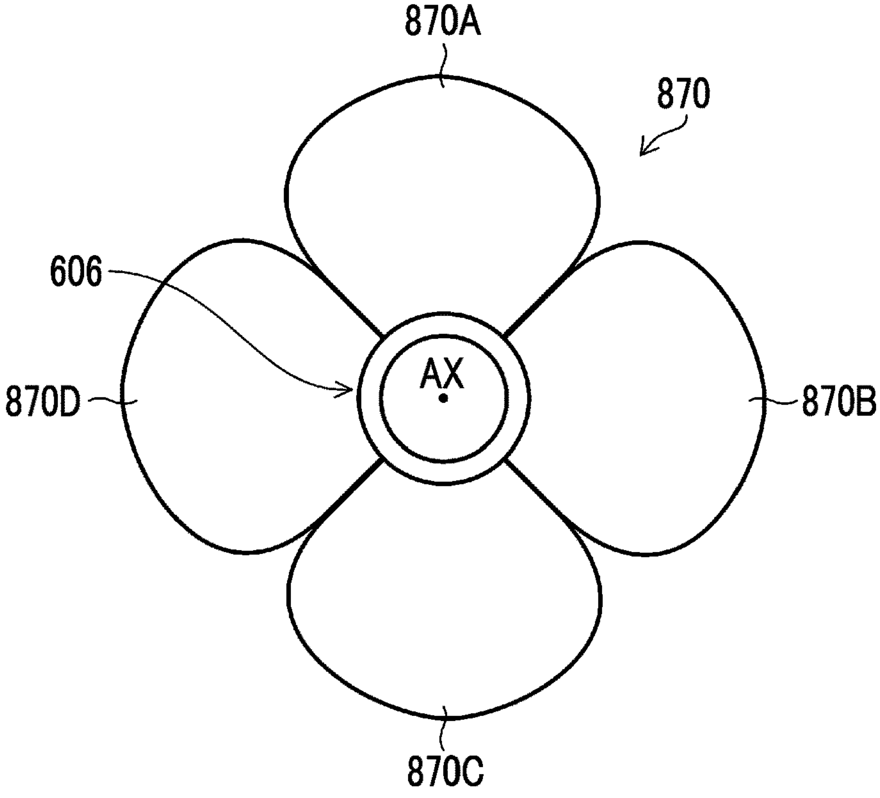
FIG. 38 is a front view showing a balloon according to a sixth modification example.

FIG. 38 is a front view showing a balloon 870 according to a sixth modification example. That is, FIG. 38 is a front view of the balloon 870 in a case where the distal end of the tube main body 606 is viewed from the distal end side of the tube main body 606.

As shown in FIG. 38, the balloon 870 includes four bulging parts 870A, 870B, 870C, and 870D along an outer peripheral surface of the tube main body 606 at the distal end part of the tube main body 606. The balloon 870 is configured such that the bulging parts 870A, 870B, 870C, and 870D can be independently and respectively operated to be expandable and contractible.

With the balloon 870 shown in FIG. 38, the distal end part of the tube main body 606 can be fixed to the intestinal wall by expanding the bulging parts 870A, 870B, 870C, and 870D and closely attaching the bulging parts 870A, 870B, 870C, and 870D to the intestinal wall (not shown). Additionally, by expanding at least one bulging part of the bulging parts 870A, 870B, 870C, and 870D and closely attaching the bulging part to the intestinal wall (not shown), it is possible to adjust the orientation of the distal end part of the tube main body 606. Specifically, for example, in a case where only the bulging part 870A positioned on the upper side in FIG. 38 is expanded and closely attached to the intestinal wall, the distal end part of the tube main body 606 can be inclined downward in FIG. 38. That is, by expanding at least one bulging part of the bulging parts 870A, 870B, 870C, and 870D, the distal end part of the tube main body 606 can be inclined in four directions of up, down, left, and right in FIG. 38. Even the balloon 870 including such bulging parts 870A, 870B, 870C, and 870D can be applied as the tube main body balloon.

In FIG. 38, the balloon 870 including the four bulging parts 870A, 870B, 870C, and 870D has been described as an example of the balloon that can change the orientation of the distal end part of the tube main body 606, but the present invention is not limited thereto. That is, any balloon including at least one or more bulging parts of the bulging parts 870A, 870B, 870C, and 870D can be applied.

Another Embodiment

In the above-described embodiments, the balloons 802, 820, 830, 840, 850, 860, and 870 have been described as examples of the intracorporeal close attachment part for closely attaching the distal end part of the tube main body 606 to the inside of the body, but another embodiment of the intracorporeal close attachment part will be described below with reference to FIGS. 39 and 40.

Figure 39:
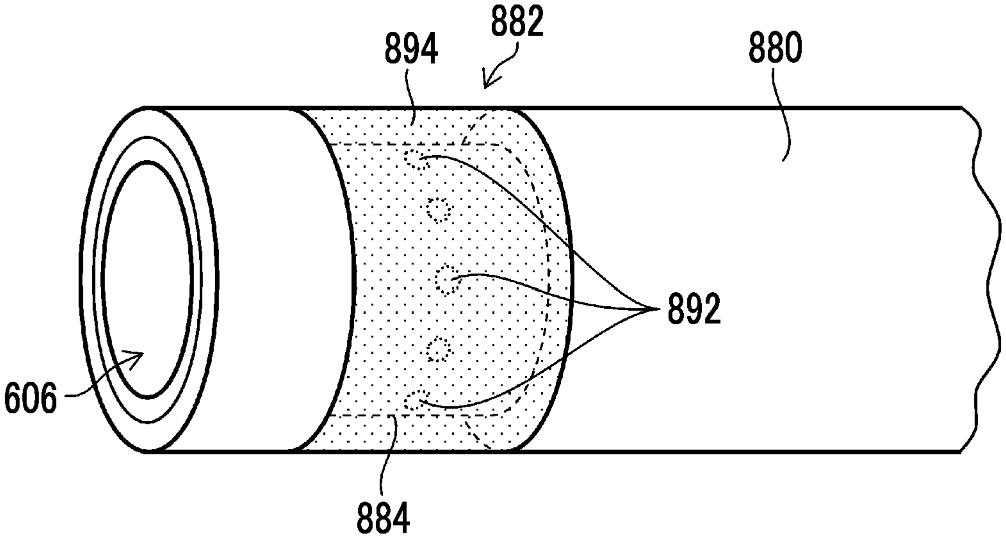
FIG. 39 is a perspective view of a main part of a tube main body to which another form of an intracorporeal close attachment part is applied.

FIG. 39 is a perspective view of a main part of the tube main body 606 to which another embodiment of the intracorporeal close attachment part is applied. FIG. 40 is a cross-sectional view of a main part of the tube main body 606 shown in FIG. 39.

Figure 40:
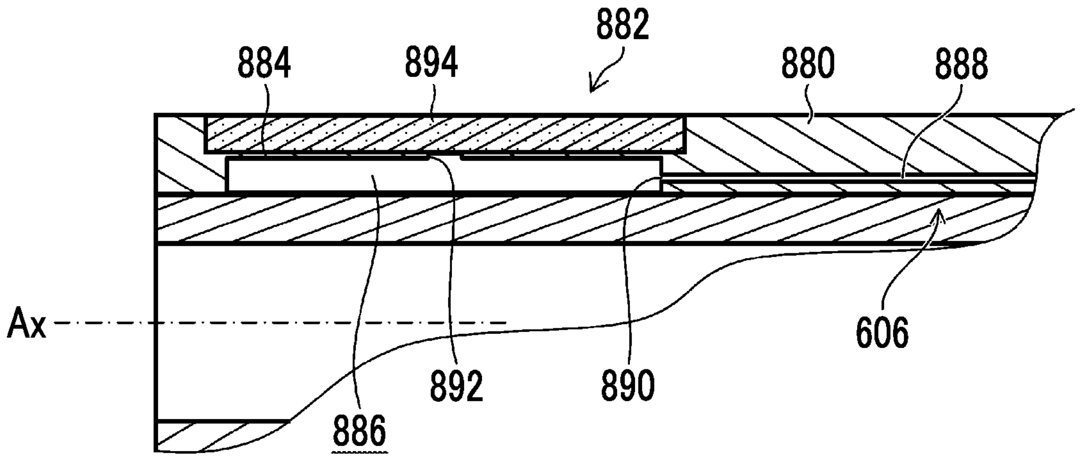
FIG. 40 is a cross-sectional view of a main part of the tube main body shown in FIG. 39.

As shown in FIG. 39 and FIG. 40, the tube main body 606 according to the present example has a tubular body 880 that accommodates the tube main body 606 inside, and an intracorporeal close attachment part 882 according to the present example is provided at the distal end part of the tubular body 880, that is, at the distal end part of the tube main body 606.

As shown in FIG. 40, a thin-wall part 884 is formed at a distal end part of the tubular body 880. The thin-wall part 884 is formed along a circumferential direction of the tubular body 880, and a suction port 892, which will be described later, is formed in the thin-wall part 884. The thin-wall part 884 has a diameter that is smaller than an outer diameter of the tubular body 880 and that is larger than an inner diameter of the tubular body 880, and a sealed space 886 is formed between the thin-wall part 884 and the tube main body 606.

As shown in FIG. 40, a multi-lumen tube 888 is formed in the tubular body 880 along the axis Ax. A distal end of the multi-lumen tube 888 is open to a sealed space 886 and formed as an air suction port 890. In addition, a proximal end of the multi-lumen tube 888 is connected to a suction pump (not shown).

As shown in FIG. 39, a plurality of suction ports 892 are arranged along a circumferential direction of the thin-wall part 884. Therefore, the intracorporeal close attachment part 882 according to the present example includes the suction port 892 arranged at the distal end part of the tube main body 606.

Further, as shown in FIG. 40, the intracorporeal close attachment part 882 includes a soft sponge member 894 that covers the suction port 892. The sponge member 894 is formed in a tubular shape, and is mounted on the distal end part of the tubular body 880 that is recessed by forming the thin-wall part 884.

With the intracorporeal close attachment part 882 configured as described above, in a case where air is sucked from the suction pump, intestinal air is sucked from the plurality of suction ports 892 into the multi-lumen tube 888 via the sealed space 866. By this suction operation, the distal end part of the tube main body 606 is closely attached to the intestinal wall (not shown) via the tubular body 880 (sponge member 894). As a result, the distal end part of the tube main body 606 is fixed inside the body. As described above, the distal end part of the tube main body 606 can be closely attached to the inside of the body even with the intracorporeal close attachment part 882 including the suction port 892.

In addition, since the intracorporeal close attachment part 882 according to the embodiment includes the sponge member 894, the intestinal wall is sucked to the suction port 892 via the sponge member 894. As a result, the intestinal wall can be protected from a peripheral part (edge part) of the suction port 892 as compared with a case where the intestinal wall is directly sucked by the suction port 892. The sponge member 894 is not an essential member, but is preferably provided from the viewpoint of protecting the intestinal wall as described above. The sponge member 894 is an example of a porous entanglement prevention member according to the embodiment of the present invention, but instead of the sponge member 894, for example, a hard (for example, metal) porous body (for example, porous metal) may be applied. However, since the sponge member 904 functions as a cushion material with respect to the intestinal wall in a case where the tube main body 606 is fixed inside the body, the sponge member 904 can be applied more preferably than the hard porous body.

In each of the above-described embodiments, the example in which the endoscope including the insertion part is applied as the medical instrument guided by the medical instrument guide device according to the embodiment of the present invention has been described, but the present invention is not limited thereto, and for example, the present invention can be applied to a medical treatment tool such as a manipulator.

Although the examples of the medical instrument guide device and the endoscope apparatus according to the embodiment of the present invention have been described above, the present invention may be improved or modified in several ways without departing from the gist of the present invention.

EXPLANATION OF REFERENCES

1: endoscope apparatus
10: guide tube
10A: distal end opening
12: endoscope
14: insertion part
16: hand operating part
18: distal end hard part
20: bendable part
22: soft part
24: illumination window
26: observation window
28: shape deformable body
28A: shape deformable body
28B: shape deformable body
28C: shape deformable body
28D: shape deformable body
28E: shape deformable body
30: outer tube
32: inner tube
34: tube main body
36: inner space
38: pump
40: pipe
42: articulated ring member
42A: articulated ring member
42B: articulated ring member
46: fixing ring member
48: articulated piece
49: fixing piece
50: piece body
52: coupling member
54: high friction surface
56: mesh-like tube
60: guide tube
70: guide tube
80: guide tube
90: guide tube
100: guide tube
104: spiral tube
106: band-shaped member
142: articulated ring member
142A: articulated ring member
142B: articulated ring member
242: articulated ring member
242A: articulated ring member
242B: articulated ring member
342: articulated ring member
342A: articulated ring member
342B: articulated ring member
442: articulated ring member
442A: articulated ring member
442B: articulated ring member
500: large intestine
502: sigmoid colon
504: transverse colon
506: lesion portion
600: guide tube
602: outer tube
604: inner tube
606: tube main body
608: inner space
610: hydrophilic coating
612: shape deformable body
614: interlayer
616: cap
618: cap
620: adhesive
622: adhesive
624: adhesive
626: adhesive
628: ventilation hole
630: three way stopcock
630A: first port
630B: second port
630C: third port
632: cock
634: valve
640: spiral tube
642: band-shaped member
644: high friction surface
650: sheet material
652: sheet
654: adhesive
656: high friction surface
700: spiral tube
702: band-shaped member
710: spiral tube
712: band-shaped member
720: spiral tube
722: band-shaped member
730: spiral tube
732: band-shaped member
734: bent part
736: bent part
740: spiral tube
742: band-shaped member
744: protrusion
746: protrusion
750: guide tube
800: endoscope apparatus

802: balloon
802A: bulging part
802B: attachment part
804: balloon
804A: bulging part
804B: attachment part
806: thread
808: air tube
810: air supply and suction port
812: pump
814: air tube
816: air supply and suction port
820: balloon
820A: bulging part
820B: bulging part
820C: attachment part
822: air tube
824: air supply and suction port
830: balloon
830A: bulging part
830B: attachment part
832: air tube
834: air supply and suction port
840: balloon
840A: bulging part
840B: attachment part
842: tubular body
844: space
846: air supply and suction port
850: balloon
850A: bulging part
852: tubular body
854: space
860: balloon
860A: bulging part
862: tubular body
864: multi-lumen tube
866: sealed space
868: air supply and suction port
870: balloon
870A: bulging part
870B: bulging part
870C: bulging part
870D: bulging part
880: tubular body
882: intracorporeal close attachment part
884: thin-wall part
886: sealed space
888: multi-lumen tube
890: air suction port
892: suction port
894: sponge member
A: first articulated piece
Ax: axis
a: first articulated piece end part region
B: second articulated piece
b: second articulated piece end part region
D: first articulated piece group
E: second articulated piece group
T: thickness
t: thickness
f: band width
G: longitudinal axis
Q: stomach
R: pylorus
S: duodenum
U: small intestine
Z: lesion portion

What is claimed is:

1. A medical instrument guide device that guides a medical instrument into a body, the medical instrument guide device comprising:

a tube main body that includes an outer tube having flexibility and an inner tube having flexibility and being arranged inside the outer tube;

a shape deformable body that is provided between the outer tube and the inner tube and is deformable along a shape of the tube main body; and an interlayer that is provided between the outer tube and the inner tube and is contactable with the shape deformable body, wherein a first contact surface that is provided on the shape deformable body and a second contact surface that is provided on the interlayer and faces the first contact surface are provided, and at least a part of any one contact surface of the first contact surface or the second contact surface includes a high friction surface.

2. The medical instrument guide device according to claim 1, wherein the interlayer is provided between the outer tube and the shape deformable body.

3. The medical instrument guide device according to claim 1, wherein the high friction surface is provided on the second contact surface.

4. The medical instrument guide device according to claim 1, wherein the high friction surface is provided on the first contact surface.

5. The medical instrument guide device according to claim 1, wherein the interlayer has a higher elastic modulus than the outer tube and the inner tube.

6. The medical instrument guide device according to claim 5, wherein the interlayer is formed by forming a sheet material into a cylindrical shape.

7. The medical instrument guide device according to claim 1, further comprising:

a fluid supply and discharge unit that supplies and discharges a fluid to and from an inner space between the outer tube and the inner tube, wherein, in a case where the fluid in the inner space is discharged by the fluid supply and discharge unit, in the tube main body, a shape of the shape deformable body is held by frictional engagement between the shape deformable body and the interlayer via the high friction surface.

8. The medical instrument guide device according to claim 1, wherein the high friction surface is a resin layer in which the one contact surface is coated with a resin.

9. The medical instrument guide device according to claim 1, wherein the high friction surface is a rough surface formed on the one contact surface.

10. The medical instrument guide device according to claim 1, wherein the high friction surface is a resin layer in which a rough surface formed on the one contact surface is coated with a resin.

11. The medical instrument guide device according to claim 1, wherein the shape deformable body includes a spiral tube formed by spirally winding a band-shaped member around an outer peripheral side of the inner tube.

12. The medical instrument guide device according to claim 1, wherein at least one surface of an outer peripheral surface of the outer tube or an inner peripheral surface of the inner tube has a hydrophilic coating.

13. An endoscope apparatus comprising:

a medical instrument; and the medical instrument guide device according to claim 1, wherein the medical instrument is an endoscope having an insertion part to be inserted into a body.

14. The endoscope apparatus according to claim 13, wherein the insertion part is able to be inserted into the tube main body, and in a state in which the insertion part is inserted into the tube main body, a clearance for preventing a body tissue from being interposed is formed between the tube main body and the insertion part.

15. The endoscope apparatus according to claim 14, wherein the clearance is 4 mm or less.

16. The endoscope apparatus according to claim 13, wherein the insertion part has an effective length that is longer than an entire length of the tube main body by 300 mm or more.

17. The endoscope apparatus according to claim 13, wherein the insertion part includes an insertion part balloon that is expandable and contractible and is provided at a distal end part of the insertion part.

18. A medical instrument guide device that guides a medical instrument into a body, the medical instrument guide device comprising:

a tube main body that includes an outer tube having flexibility and an inner tube having flexibility and being arranged inside the outer tube; and a shape deformable body that is provided between the outer tube and the inner tube and is deformable along a shape of the tube main body, wherein a first contact surface that is provided on the shape deformable body and a second contact surface that is provided on at least one tube of the outer tube or the inner tube and faces the first contact surface are provided, and at least a part of any one contact surface of the first contact surface or the second contact surface includes a high friction surface.

19. The medical instrument guide device according to claim 18, further comprising:

a fluid supply and discharge unit that supplies and discharges a fluid to and from an inner space between the outer tube and the inner tube, wherein, in a case where the fluid in the inner space is discharged by the fluid supply and discharge unit, in the tube main body, a shape of the shape deformable body is held by frictional engagement between the shape deformable body and the one tube via the high friction surface.

* * * * *